(12) United States Patent
Kurth et al.

(10) Patent No.: US 10,716,920 B2
(45) Date of Patent: Jul. 21, 2020

(54) TRANSSEPTAL PUNCTURE APPARATUS AND METHOD FOR USING THE SAME

(71) Applicant: Pressure Products Medical Supplies Inc., Santa Barbara, CA (US)

(72) Inventors: Paul Kurth, Santa Barbara, CA (US); Andrew Armour, Swarthmore, PA (US); Andrzej J. Chanduszko, Weymouth, MA (US); Carol A. Devellian, Topsfield, MA (US)

(73) Assignee: AECORSIS B.V., Haarlem (NL)

( * ) Notice: Subject to any disclaimer, the term of this patent is extended or adjusted under 35 U.S.C. 154(b) by 227 days.

(21) Appl. No.: 15/811,080

(22) Filed: Nov. 13, 2017

(65) Prior Publication Data

US 2018/0064915 A1    Mar. 8, 2018

Related U.S. Application Data

(60) Division of application No. 14/638,537, filed on Mar. 4, 2015, now Pat. No. 9,821,145, which is a (Continued)

(51) Int. Cl.
*A61B 17/34* (2006.01)
*A61M 25/09* (2006.01)
(Continued)

(52) U.S. Cl.
CPC ......... *A61M 25/09* (2013.01); *A61B 17/0057* (2013.01); *A61B 17/3468* (2013.01); *A61M 25/09041* (2013.01); *A61B 2017/00243* (2013.01); *A61B 2017/00247* (2013.01); *A61B 2017/00575* (2013.01); *A61B 2017/00597* (2013.01); *A61B 2017/00606* (2013.01); (Continued)

(58) Field of Classification Search
CPC ............ A61B 17/3478; A61B 17/3468; A61B 17/0057; A61B 17/3423; A61B 2017/00243; A61B 2017/00575; A61B 2017/06095; A61M 25/09; A61M 25/09041

See application file for complete search history.

(56) References Cited

U.S. PATENT DOCUMENTS 5,100,432 A    3/1992  Matsutani
5,190,528 A    3/1993  Fonger
(Continued)

FOREIGN PATENT DOCUMENTS

WO    WO2013101632    7/2013
WO    WO2014182969    11/2014

*Primary Examiner* — Tuan V Nguyen
(74) *Attorney, Agent, or Firm* — Marcus C. Dawes

(57) ABSTRACT

Devices and methods for performing a transseptal puncture procedure using a device which includes either an untapered or tapered blunt end cannula disposed in an introducer carrying a sharp guidewire disposed longitudinally through the lumen of the blunt cannula, and a blunt end dilator wherein the guidewire is flexible and has an atraumatic shape at its tip. The cannula gives the more flexible introducer a defined shape and steerabilty allowing an ordinarily skilled physician to easily access a selected location on the septal wall of the heart for transseptal puncture and introducer placement thereacross without employing an exposed sharp end needle during the procedure.

21 Claims, 30 Drawing Sheets

Related U.S. Application Data continuation-in-part of application No. 13/428,719, filed on Mar. 23, 2012, now Pat. No. 8,992,556.

(51) Int. Cl.
  *A61B 17/00* (2006.01)
  *A61M 25/01* (2006.01)
  *A61B 17/06* (2006.01)
  *A61B 17/22* (2006.01)

(52) U.S. Cl.
  CPC ......... *A61B 2017/00623* (2013.01); *A61B 2017/00991* (2013.01); *A61B 2017/06095* (2013.01); *A61B 2017/22047* (2013.01); *A61M 2025/0177* (2013.01)

(56) References Cited

U.S. PATENT DOCUMENTS

| | | |
|---|---|---|
| 8,992,556 B2 | 3/2015 | Chanduszko |
| 2002/0169377 A1 | 11/2002 | Khairkhahan |
| 2003/0163153 A1* | 8/2003 | Scheib ............ A61B 17/3478 606/191 |
| 2003/0208141 A1* | 11/2003 | Worley ............ A61M 25/0041 600/585 |
| 2005/0065507 A1 | 3/2005 | Hartley |
| 2008/0101984 A1* | 5/2008 | Saini .................. G01N 21/69 422/52 |
| 2009/0105742 A1 | 4/2009 | Kurth |
| 2009/0171276 A1 | 7/2009 | Bednarek |
| 2010/0114140 A1 | 5/2010 | Chanduszko |
| 2011/0004220 A1 | 1/2011 | Krueger |
| 2013/0123620 A1* | 5/2013 | Tekulve ............ A61B 17/3478 600/435 |

\* cited by examiner

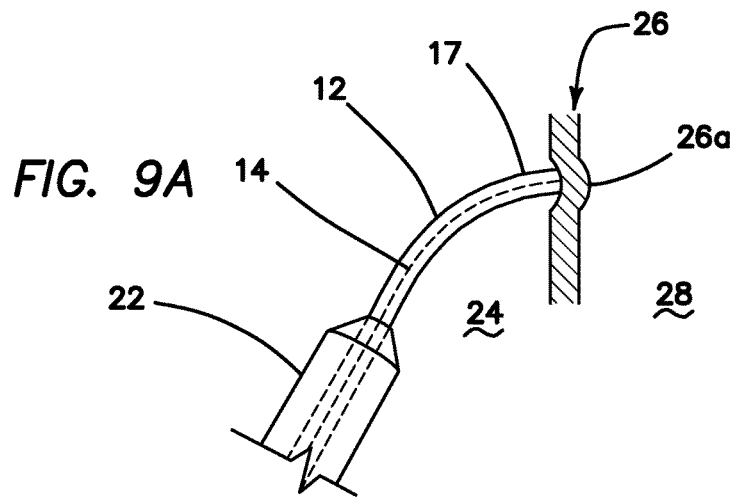
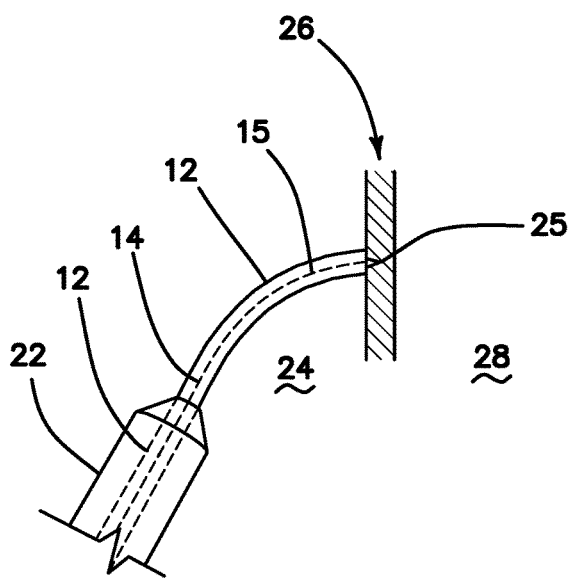
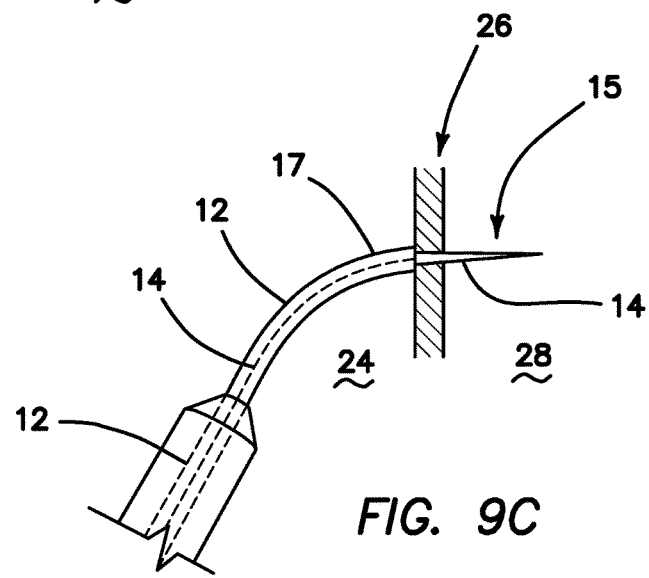

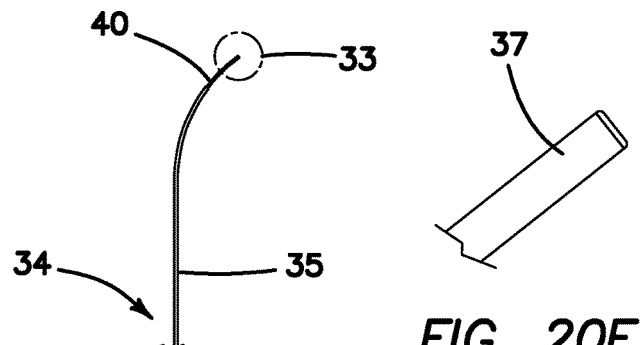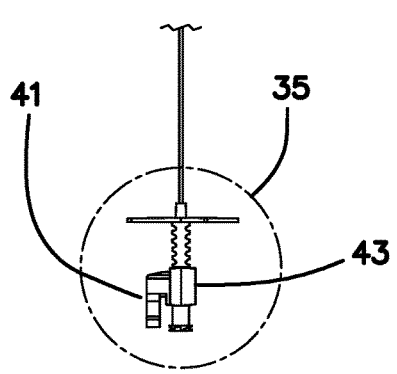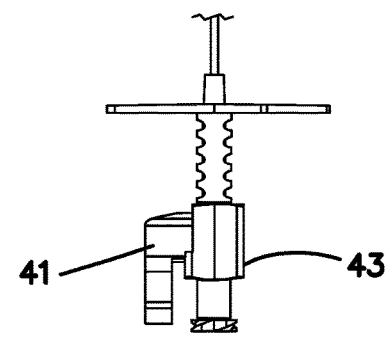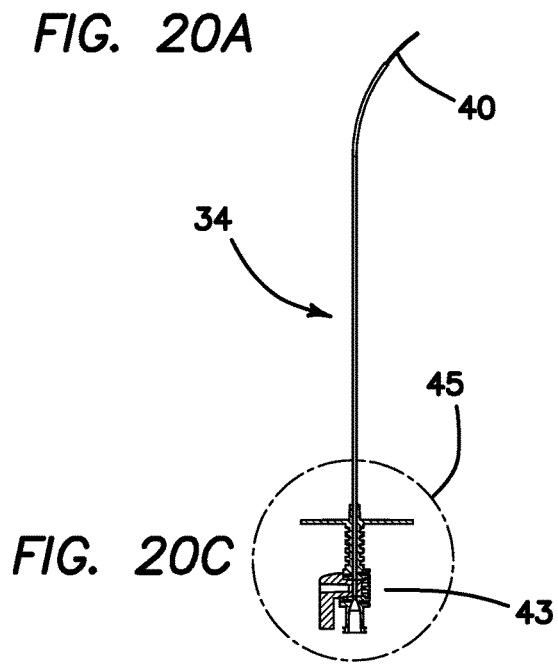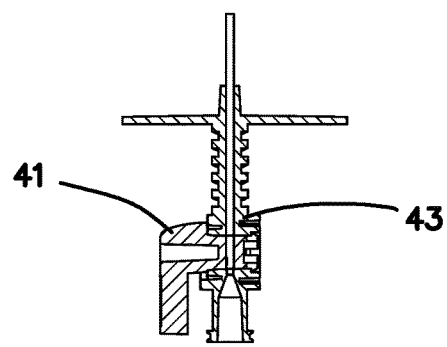
FIG. 20E
FIG. 20B
FIG. 20A
FIG. 20C
FIG. 20D

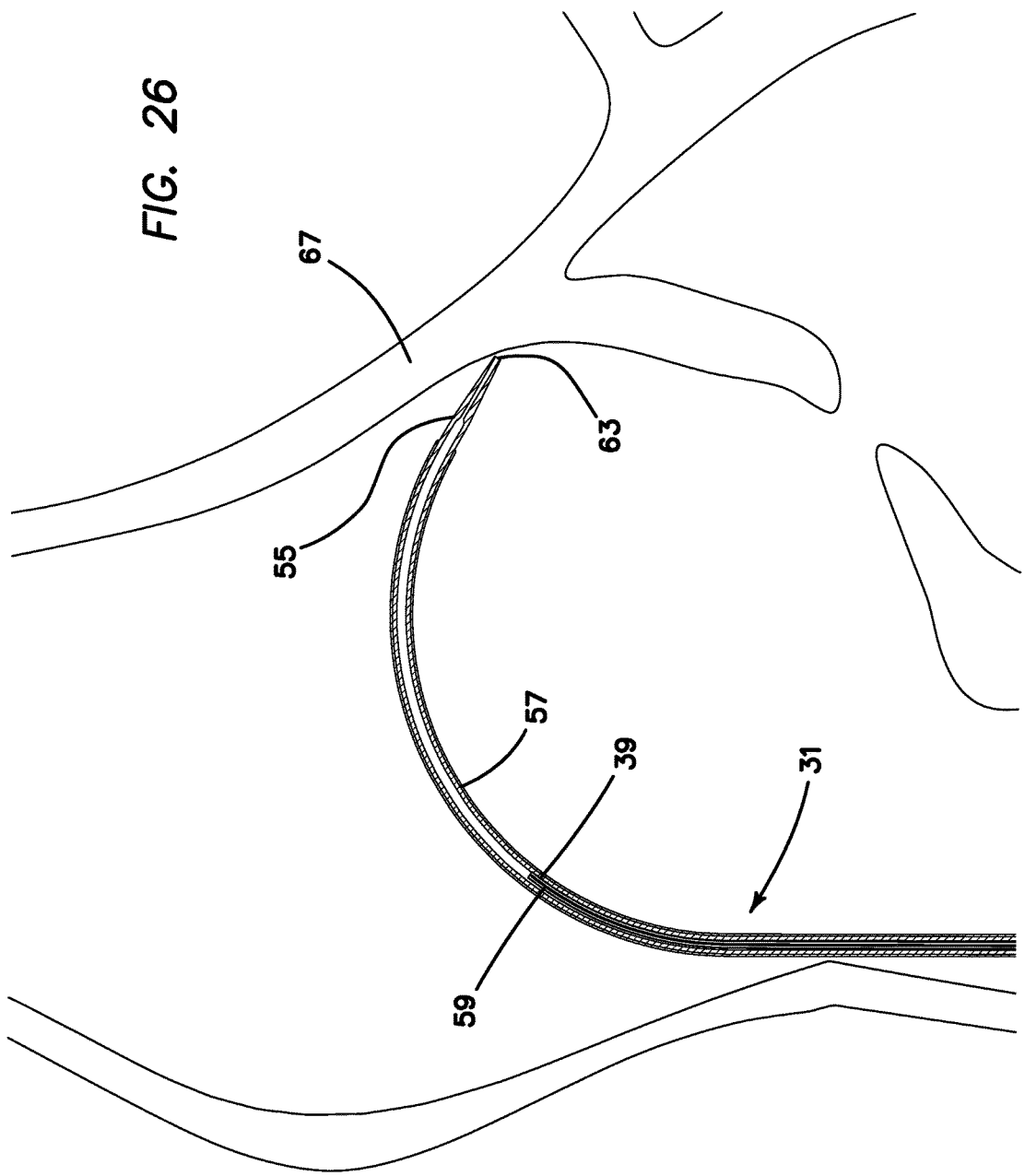

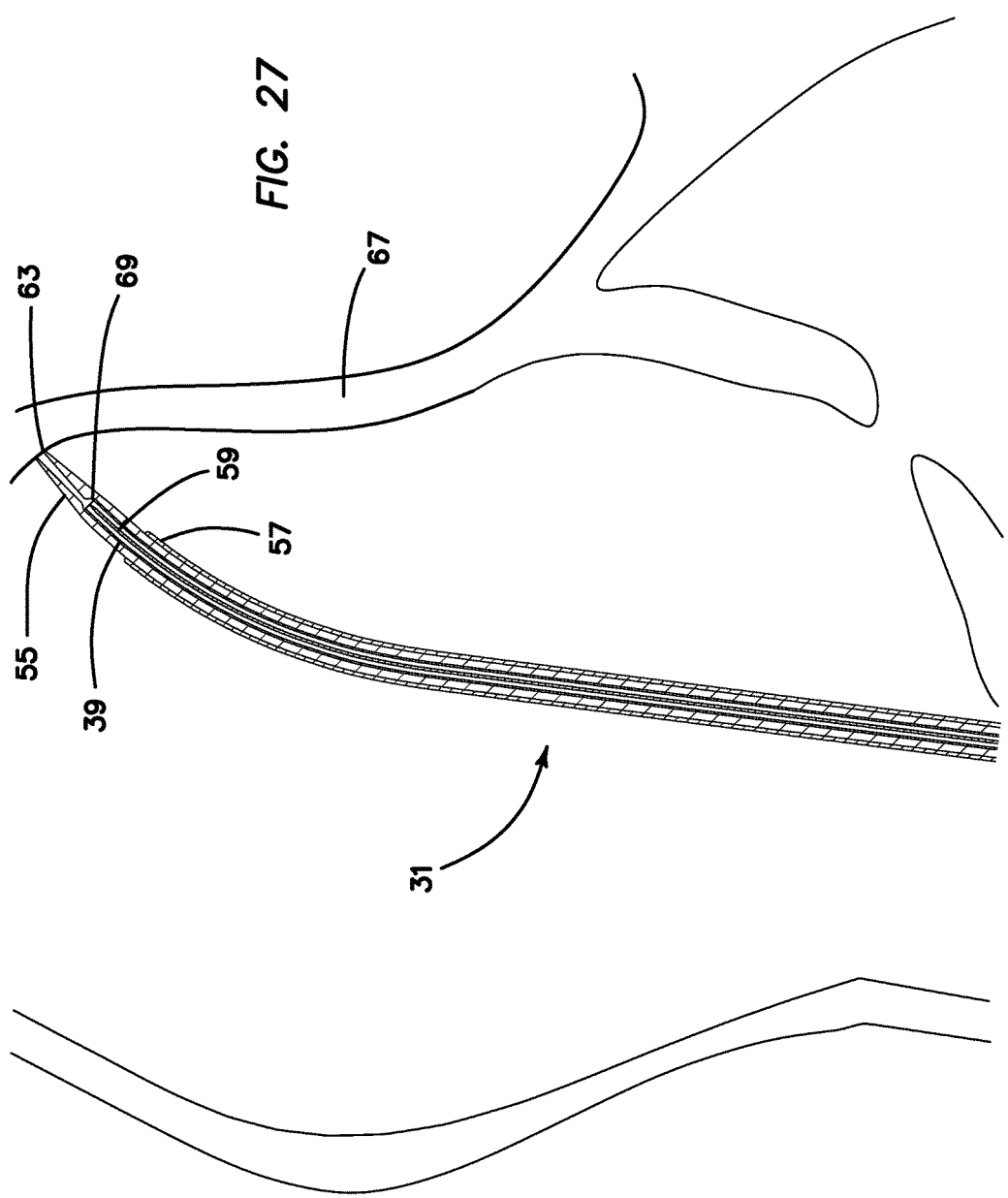

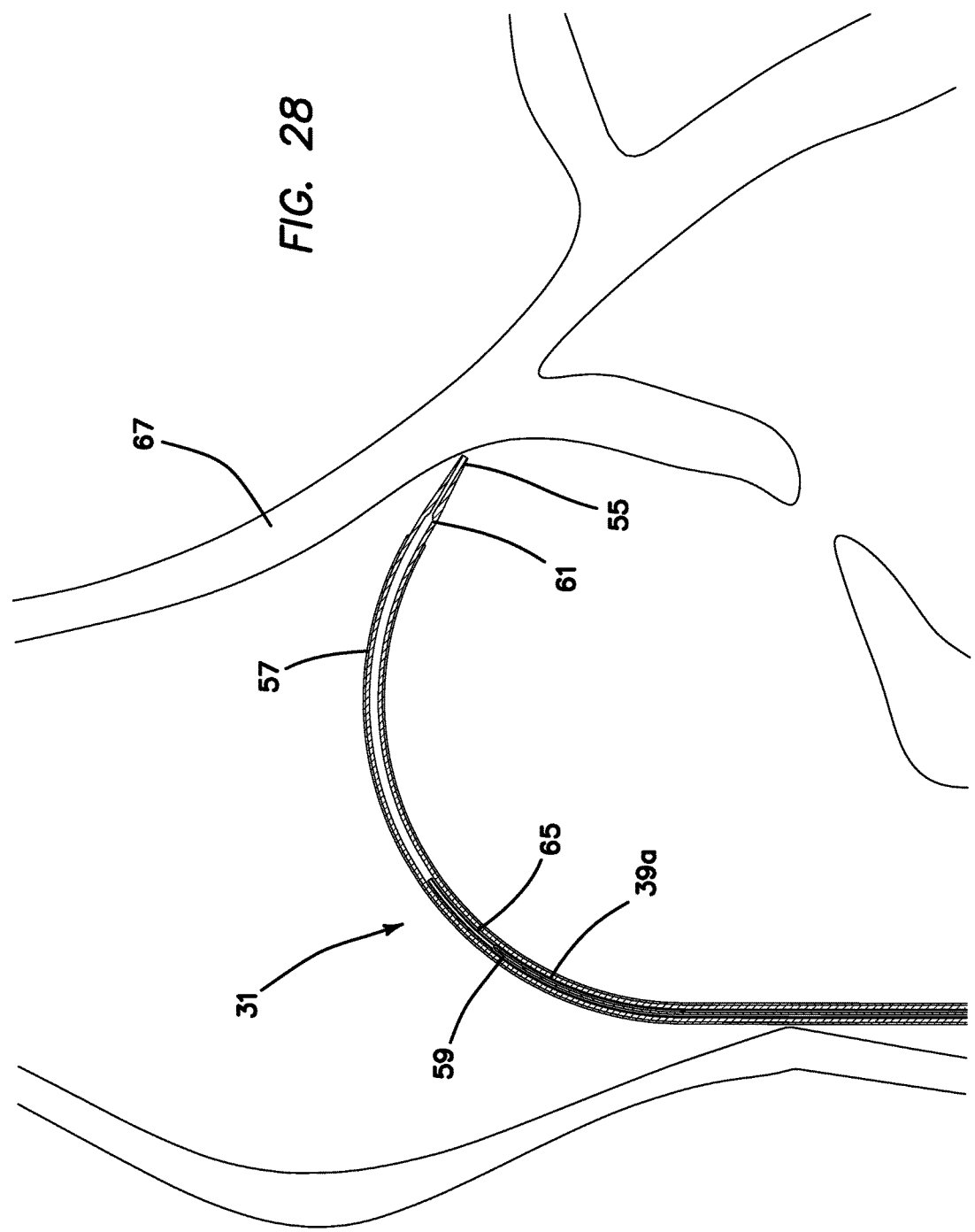

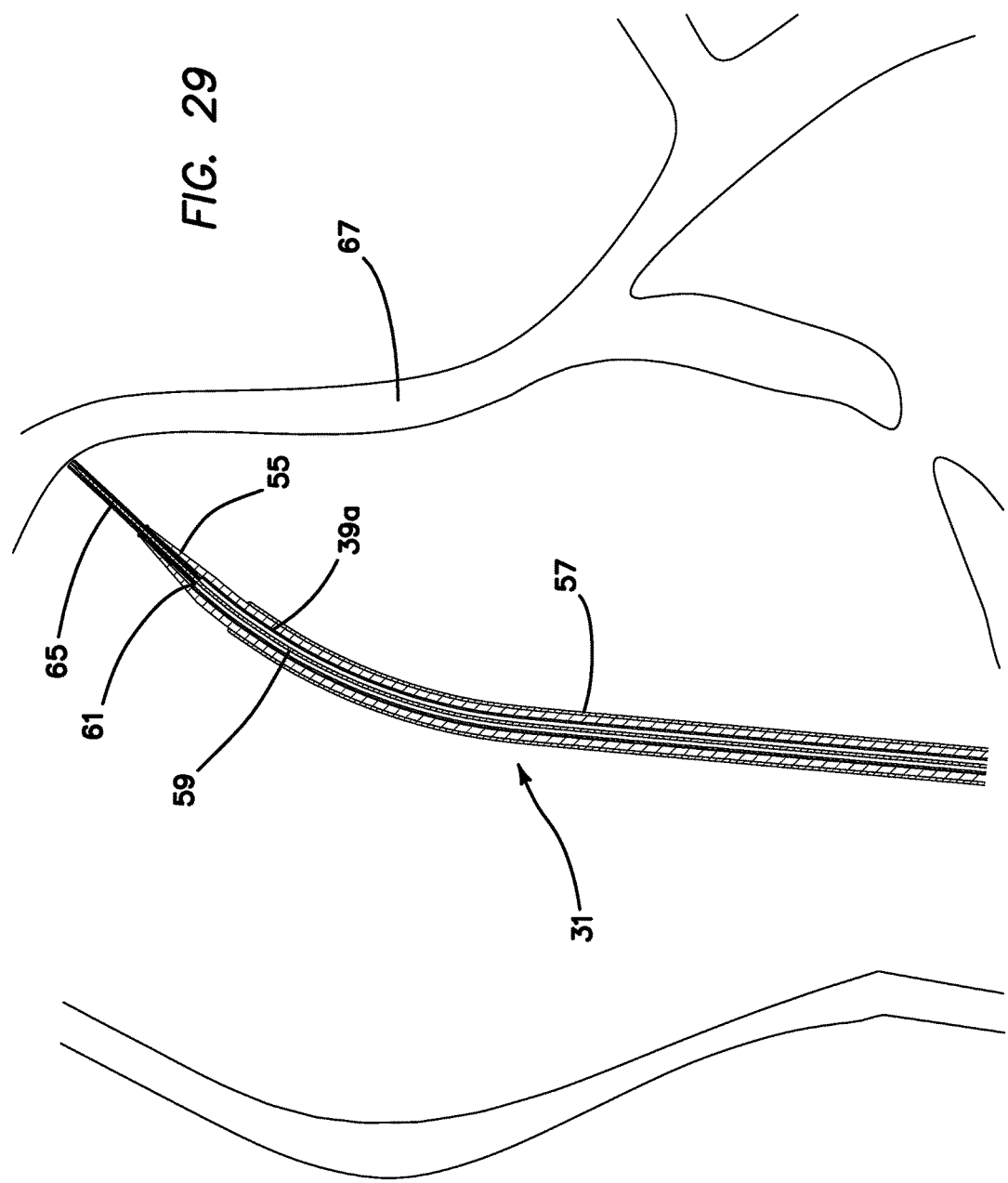

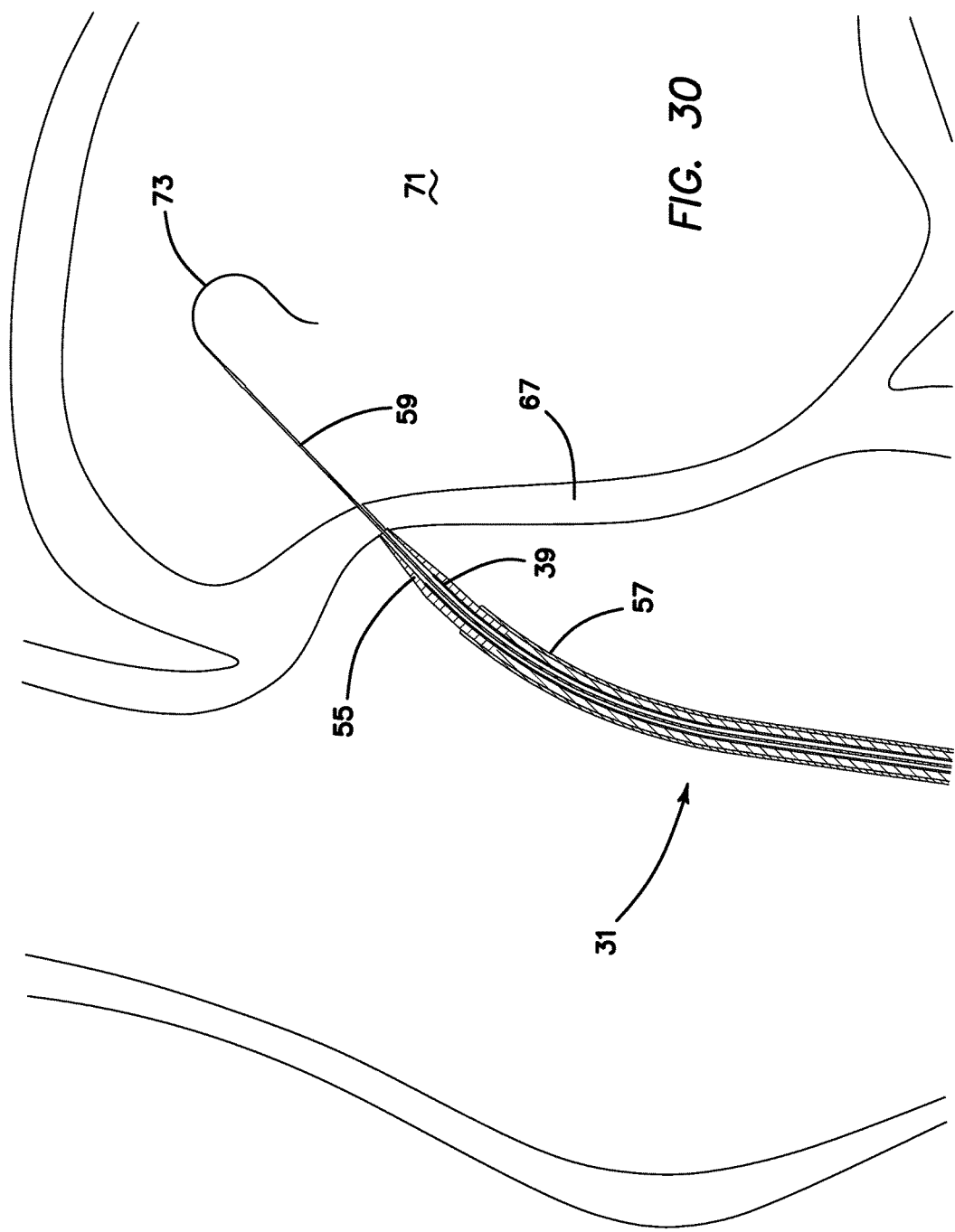

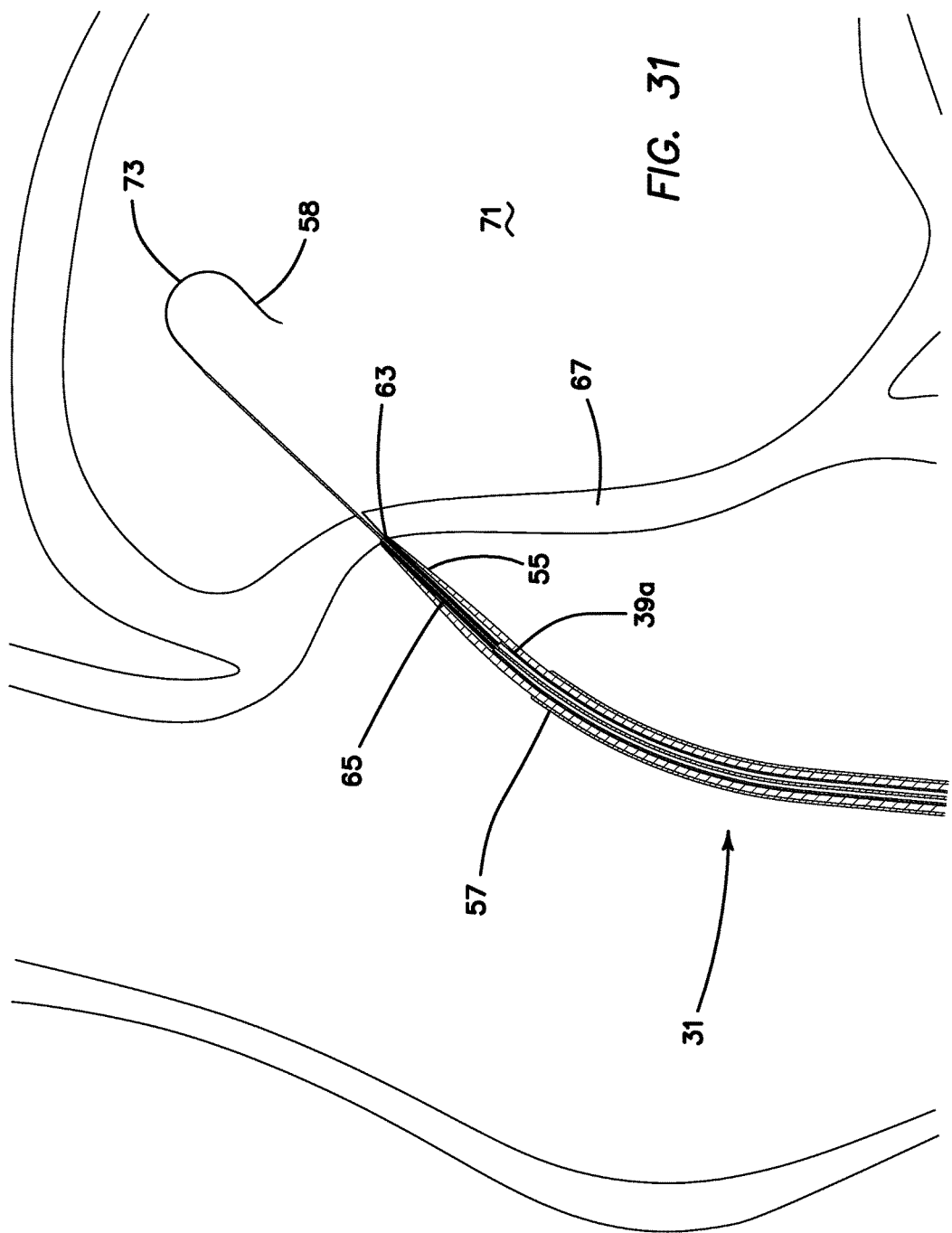

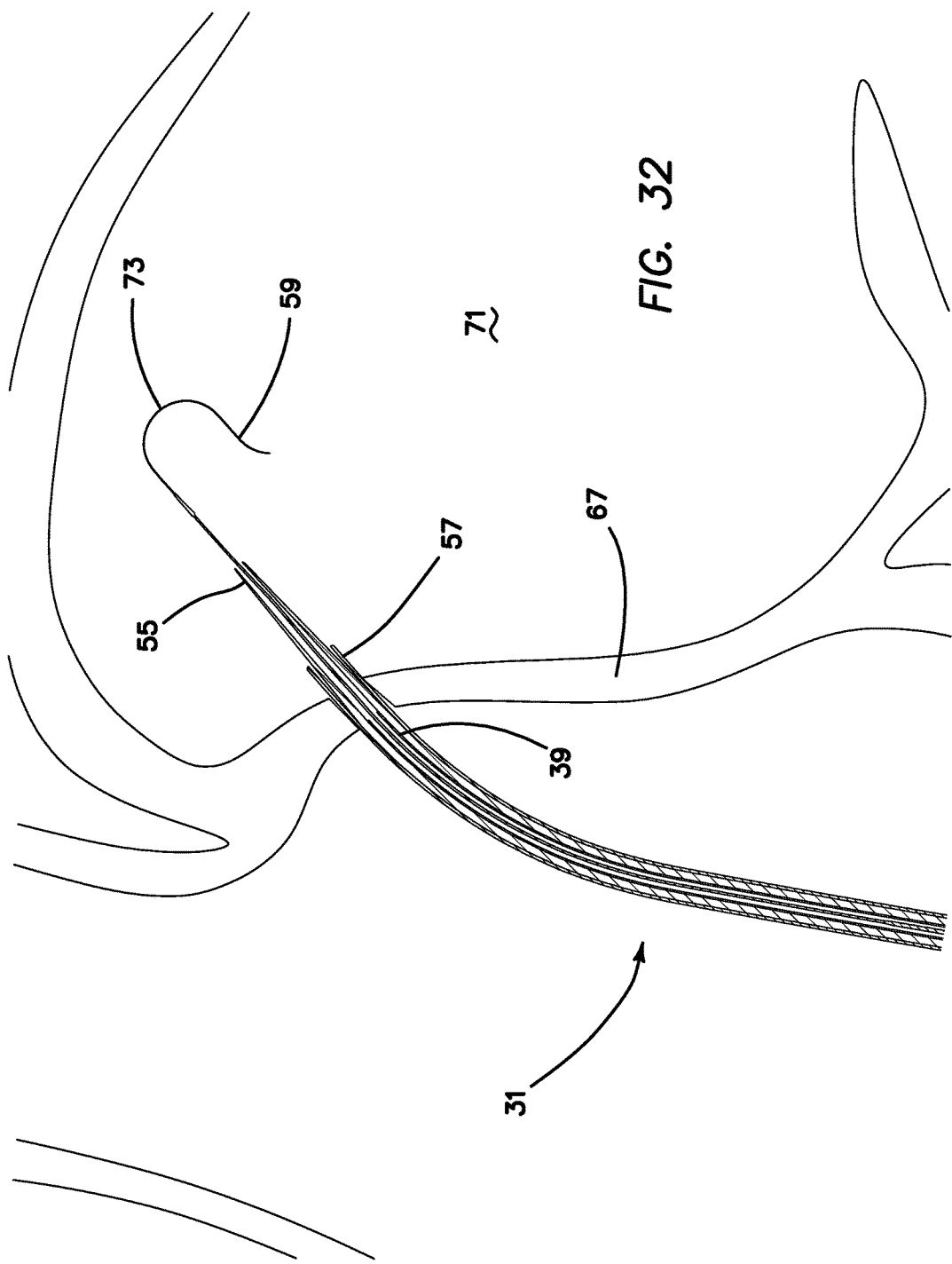

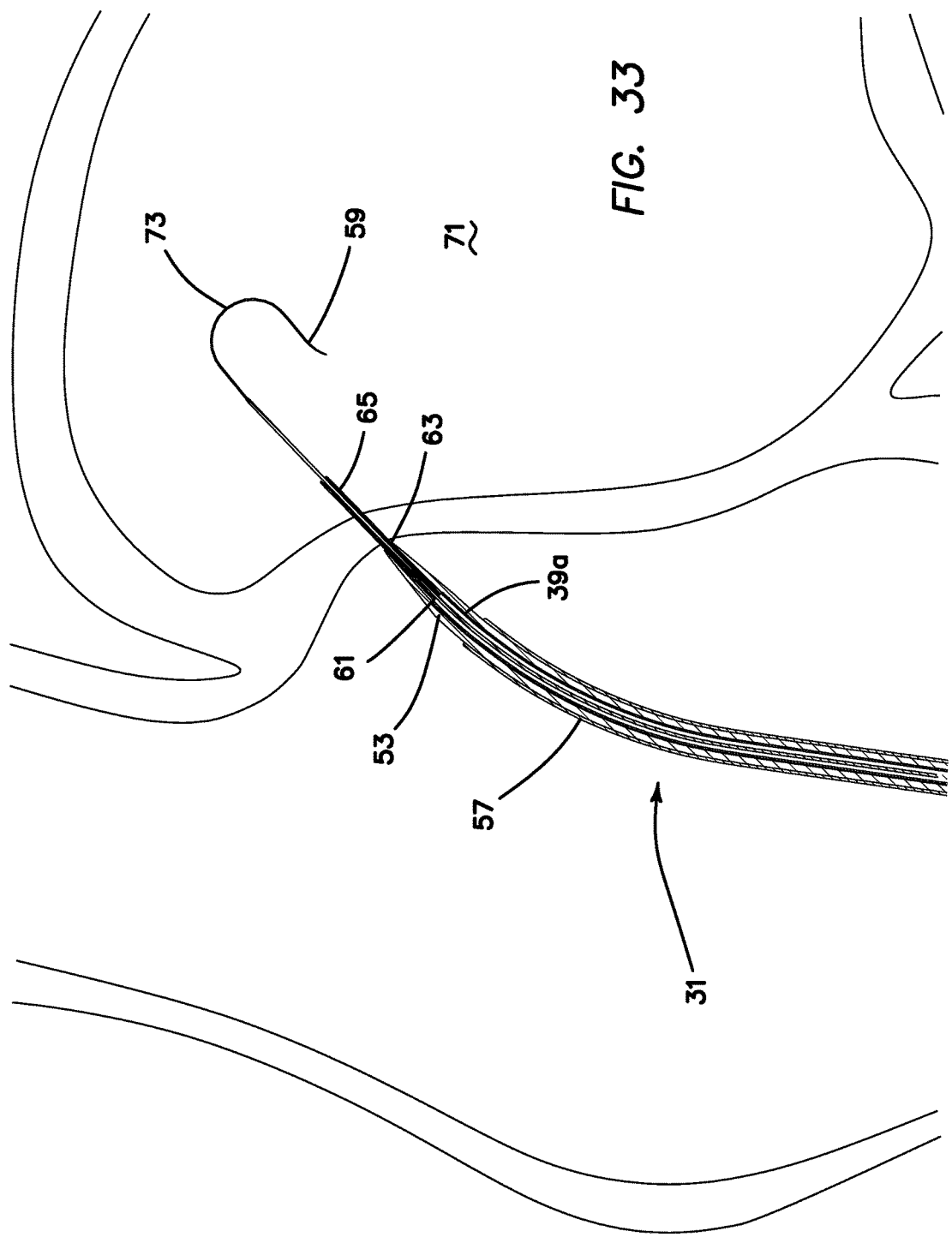

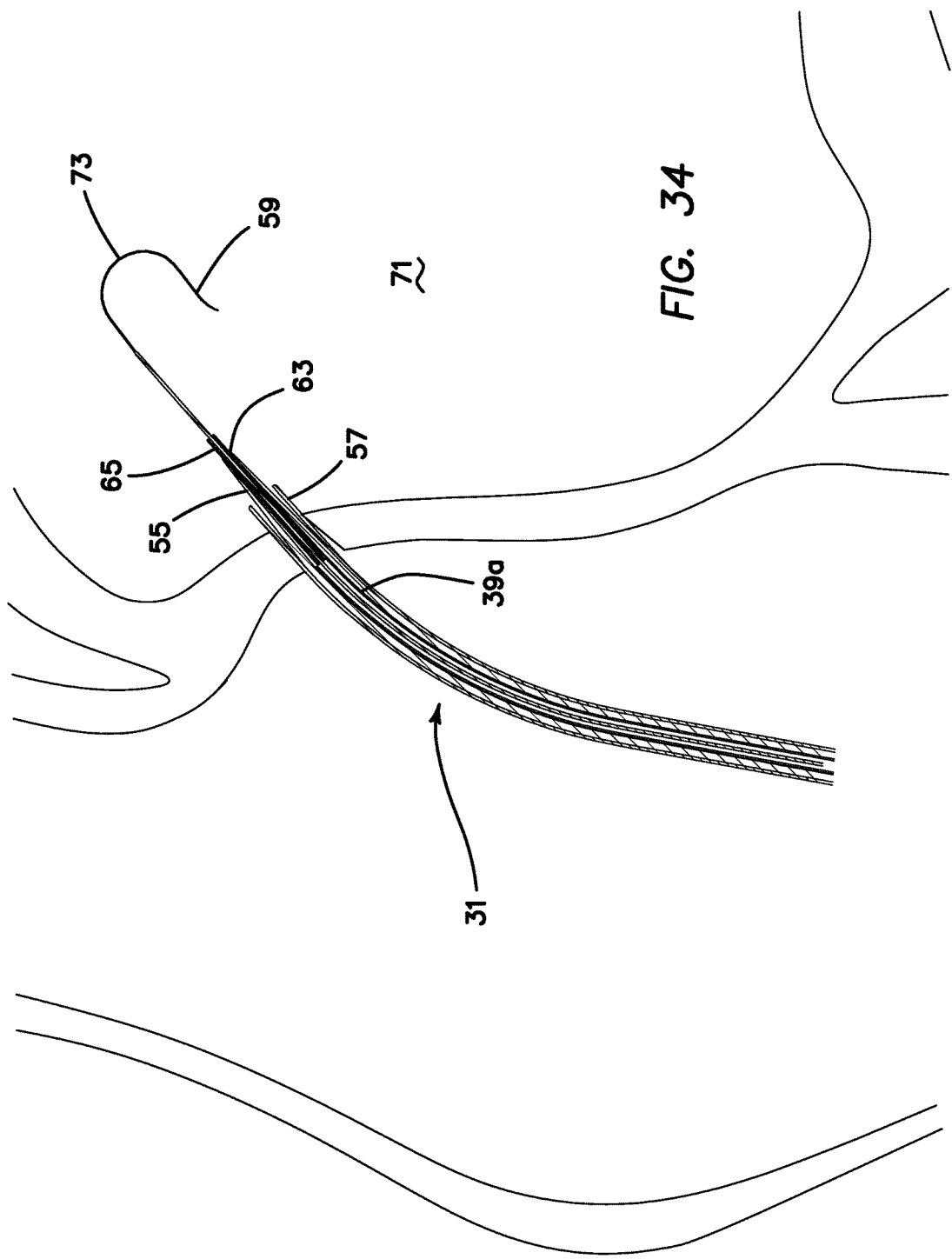

TRANSSEPTAL PUNCTURE APPARATUS AND METHOD FOR USING THE SAME

RELATED U.S. PATENT DOCUMENTS

This application claims pursuant to 35 USC 120 priority to, the benefit of and is a divisional application of U.S. patent application Ser. No. 14/638,537, filed on Mar. 4, 2015, and soon to be issued as U.S. Pat. No. 9,821,145 and which is incorporated herein in its entirety by reference.

FIELD OF THE INVENTION

The invention generally relates to a device for performing an intracardiac transseptal puncture procedure.

BACKGROUND OF THE INVENTION

Septal puncture through an intact atrial septum from the right atrium to the left atrium is often necessary. This is traditionally performed using rigid, long needles, such as Brockenbrough or Ross needles. In all types of septal puncture, the needle that is used to puncture the atrial septum poses a high risk of inadvertent puncture through tissue other than the septum primum, for example, the atrial free wall, posing a significant risk to the patient. For patent foramen ovale (PFO) closure, this risk is potentially even higher, due to the fact that the septal tissue is defective and often thinning, and may stretch an even greater amount during the puncture procedure, bringing the tip of the needle dangerously close to the atrial free wall or the left atrial appendage.

The currently offered SafeSept® Transseptal Guidewire by Pressure Products Medical Supplies Inc. provides a sharp but atraumatic curved guidewire that is fed through a sharp transseptal needle disposed within an introducer. The introducer includes an outer sheath and a tapered dilator which telescopes out of the sheath. The transseptal needle in turn is disposed into the dilator. The tapered dilator is used to tent the septum without the needle extending beyond the distal tip of the tapered dilator, the sharp guidewire is advanced out of the dilator to penetrate the septum as its column is supported by the needle. Because of the columnar support, the guidewire is able to penetrate the septum without bending or buckling the otherwise flexible guidewire. Without such columnar support, the guidewire would not have the columnar strength to be pushed through the septum. Once the guidewire has penetrated the septum, the sharp needle is advanced out of the dilator over the guidewire through the septum into the left atrium. The dilator is advanced over the needle, then the sheath is advanced over the dilator into the left atrium. With the sheath safely in place, the tapered dilator, needle, and guidewire are removed so that a catheter or other cardiac instrument may be introduced into the left atrium through the sheath.

In the SafeSept® Transseptal Guidewire Needle Free produced by Pressure Products the method of septal penetration is the same as with the SafeSept® Transseptal Guidewire, but no transseptal needle is provided. Only the atraumatic sharp guidewire is used to penetrate the septum and the tapered dilator is advanced over the guidewire into the left atrium. Because no needle is employed, it is possible that both the tapered dilator and sheath may be able to be advanced through the septum by the use of an oscillating rotation of the tapered dilator and/or sheath as it is being advanced.

SUMMARY OF THE INVENTION

The illustrated embodiments include a transseptal instrument for accessing a cardiac septal wall within a heart which includes a flexible introducer having an interior lumen, a distal curve, and a distal taper; and a cannula having an interior lumen, a distal curve, and a distal blunt end, the cannula being telescopically disposed into the flexible introducer. The flexible introducer has insufficient columnar strength and unsuitable shape for accessing a predetermined location on the cardiac septal wall when the cannula is not disposed within the interior lumen of the introducer and in close proximity to the distal taper thereof, but is able to access the predetermined location on the cardiac septal wall when the cannula is disposed within the interior lumen of the introducer and in close proximity to the distal taper thereof.

The flexible introducer includes a blunt tapered end outer sheath and a blunt tapered end dilator telescopically disposed in the outer sheath. Throughout the balance of this specification, reference shall be made to a blunt needle, although the term blunt dilator could be applied with equal accuracy in cases where only one of the two components is used. Therefore, wherever below "blunt needle" is used, it should be understood that a "blunt dilator" could be used instead.

In one embodiment the cannula is nontapered and is nonextendable beyond the distal taper of the introducer.

In another embodiment the cannula is tapered and is nonextendable beyond the distal taper of the introducer.

In another embodiment the cannula is tapered or necked down and is extendable beyond of the distal taper of the introducer.

In another embodiment the cannula is nontapered or necked down and is extendable beyond of the distal taper of the introducer.

The transseptal instrument further includes a sharp end floppy guidewire telescopically disposed within the interior lumen of the cannula. The guidewire is prebiased to assume an atraumatic configuration when unsupported, but has sufficient columnar strength when supported to be capable of being pushed through a tough fibrous septal wall.

In one embodiment the guidewire when first extended beyond the distal blunt end of the cannula is supported by the cannula.

In another embodiment the guidewire when first extended beyond the distal taper of the introducer is supported by the cannula and/or distal taper of the introducer.

The illustrated embodiments thus include a transseptal instrument for accessing a cardiac septal wall within a heart which includes a flexible introducer having an interior lumen, a distal curve, and a distal taper; a proximal hub; a valve included within the hub; and a cannula coupled to the proximal hub and valve, the cannula having an interior lumen, a distal curve, and a distal blunt end. The cannula is telescopically disposed into a flexible introducer. The introducer has an interior lumen with a first proximal lumen inner diameter and a second smaller distal lumen inner diameter, a distal curve, and a distal taper. The distal blunt end of the cannula is able to pass through the first proximal lumen diameter but not though the second smaller distal lumen diameter of the introducer. The flexible introducer is characterized by insufficient columnar strength and unsuitable curve shape to access the cardiac septal wall unless the cannula is disposed within the lumen having the first proximal lumen inner diameter.

The flexible introducer includes a blunt end outer sheath having the first proximal lumen inner diameter, and a blunt end tapered dilator telescopically disposed in the outer sheath having the second smaller distal lumen inner diameter.

The transseptal instrument further includes a sharp end floppy guidewire telescopically disposed within the interior lumen of the cannula, the guidewire being prebiased to assume an atraumatic configuration when unsupported, but to have sufficient columnar strength when supported to be capable of being pushed through the septal wall.

The guidewire when first extended beyond the distal blunt end of the cannula is supported by the cannula.

The guidewire when first extended beyond the distal taper of the introducer is supported by the cannula and/or distal taper of the introducer.

The illustrated embodiments are thus also understood to include a transseptal instrument for accessing a cardiac septal wall within a heart which includes a flexible introducer having an interior lumen, a distal curve, and a distal taper; a proximal hub; a valve included within the hub; and a cannula coupled to a proximal hub and valve, the cannula having an interior lumen, a distal curve, and a distal blunt end. The cannula is telescopically disposed into the flexible introducer. The introducer has a stepped interior lumen with a first proximal lumen inner diameter and a second smaller distal lumen inner diameter, or an interior lumen having a tapered inner diameter. The introducer also has a distal curve, and an exterior distal taper. The distal blunt end cannula is stepped or distally tapered so as to be able to pass through the first proximal lumen diameter and the second smaller distal lumen diameter of the introducer to extend beyond the distal taper of the introducer or beyond the portion of the interior lumen having a tapered inner diameter. The flexible introducer is characterized by insufficient columnar strength and unsuitable curve shape to access the cardiac septal wall unless the cannula is disposed within the lumen having the first proximal lumen inner diameter or possibly within the interior lumen having a tapered inner diameter.

The flexible introducer includes a blunt taper end outer sheath having the first proximal lumen inner diameter, and a blunt tapered end dilator telescopically disposed in the outer sheath and having the second smaller distal lumen inner diameter or having the interior lumen with a tapered inner diameter.

The transseptal instrument further includes a sharp end floppy guidewire telescopically disposed within the interior lumen of the cannula, the guidewire being prebiased to assume an atraumatic configuration when unsupported, but to have sufficient columnar strength when supported to be capable of being pushed through the septal wall.

The guidewire when first extended beyond the distal blunt end of the cannula is supported by the cannula.

The guidewire when first extended beyond the exterior distal taper of the introducer is supported by the cannula and/or the interior lumen having a tapered inner diameter.

The illustrated embodiments of the invention further extend to a method including the steps of: telescopically disposing a blunt end cannula into a flexible introducer having an interior lumen, a distal curve, and a distal taper to define a predetermined shape and steerability to at least a distal portion of the introducer, where the flexible introducer has insufficient columnar strength and unsuitable shape for accessing a selected location on the cardiac septal wall when the cannula is not disposed within the interior lumen of the introducer and in close proximity to the distal taper thereof, but is able to access the predetermined location on the cardiac septal wall when the cannula is disposed within the interior lumen of the introducer and in close proximity to the distal taper thereof; intravascularly accessing a right atrium of a patient's heart with the introducer; steering the distal taper of the introducer to the selected location on a septal wall of the heart to tent the septal wall at the selected location; advancing a sharp ended floppy guidewire telescopically disposed within an interior lumen of the cannula while being supported by the cannula to provide sufficient columnar strength to the floppy guidewire to allow it to be pushed through the septal wall into a left atrium of the patient's heart; and advancing the sharp ended floppy guidewire beyond any support by the cannula to configure the sharp ended floppy guidewire into a prebiased atraumatic shape.

The method further includes the step of advancing the cannula through the septal wall over the guidewire.

The method further includes advancing the introducer through the septal wall over the cannula.

The method further includes advancing the introducer through the septal wall over the guidewire while leaving the cannula telescopically retained in the introducer.

In one aspect, the invention relates to a device for puncturing the atrial septum of a patient. In one embodiment of the invention, the device includes an outer needle with a blunt distal end and a lumen longitudinally defined therethrough and a guidewire axially disposed in the lumen of the needle. In one embodiment, the guidewire has a proximal portion, an intermediate portion, and a distal portion, wherein the intermediate portion is more flexible than either the proximal portion or the distal portion of the guidewire.

In an embodiment, the intermediate portion is a segment that is approximately 20 mm from the distal end of the guidewire. The intermediate portion may be, for example, 3 mm in length. In an embodiment, the intermediate portion has a waist. The waist of the intermediate portion is, for example, about 0.2 mm in diameter. In a particular embodiment, the intermediate portion of the guidewire may be made of a polymer.

In another embodiment, the guidewire has a distal portion and a proximal portion, wherein the distal portion is more flexible than the proximal portion. In another embodiment, the guidewire is flexible in both the distal portion and the proximal portion (e.g., has homogeneous flexibility).

As another feature, the distal portion of the guidewire has a distal portion that deviates from the linear path of the guidewire such as, for example, a taper, a bend, a curve, a cork screw or a hook. In a particular embodiment, the tip of the guidewire is turned inward during the delivery procedure to avoid the risk of inadvertent puncture of tissue. In another embodiment, the guidewire contains a portion that has a different thickness or diameter than the rest of the guidewire such as, for example, a tapered portion, whereby the guidewire is tapered from one thickness to another.

In an embodiment, the distal portion of the cannula is more flexible than the proximal portion of the cannula.

In still another embodiment, the device includes a cannula with a blunt distal end and a lumen axially disposed therethrough and a pump for introducing a high pressure jet spray through the lumen of the cannula.

In a further embodiment of the invention, the device has a cannula with a blunt distal end and an insulating material for insulating the length of the proximal and intermediate portion, leaving the distal tip of the cannula uninsulated. As an additional feature, the device may include unipolar electrodes or, alternatively, the device may include bipolar electrodes.

In another aspect, the invention provides a method for puncturing the atrial septum of a patient's heart by accessing the right atrium via a vessel. The method includes introducing into the right atrium a transseptal puncture device that includes a cannula with a blunt distal end and a lumen longitudinally defined therethrough and a guidewire axially disposed in the lumen of the cannula, the guidewire having a proximal portion, a distal portion, and an intermediate portion that is more flexible than the proximal portion or the distal portion. The blunt needle is contacted with the atrial septum and the guidewire is pushed through the septum in advance of the blunt needle. A delivery sheath is then positioned using a standard catheterization laboratory technique in the left atrium and the transseptal puncture device is withdrawn from the patient's body.

In another aspect, the invention provides a method for puncturing the atrial septum of a patient's heart by accessing the right atrium via a vessel. The method includes introducing into the right atrium a transseptal puncture device that includes a blunt needle with a blunt distal end and a lumen longitudinally disposed therethrough and a guidewire axially disposed in the lumen of the blunt needle, the guidewire having a proximal portion and a distal portion, wherein the distal portion is more flexible than the proximal portion. The blunt needle is first contacted with the atrial septum. The guidewire is then pushed through the septum in advance of the blunt needle. A delivery sheath is positioned in the left atrium and the transseptal puncture device is withdrawn from the patient's body.

BRIEF DESCRIPTION OF THE DRAWINGS

In the drawings, like reference numbers generally refer to the same parts throughout the different views. Also, the drawings are not necessarily to scale, emphasis instead generally being placed upon illustrating the principles of the invention.

FIG. 9a-9g depicts the steps in an illustrative method for puncturing an atrial septum with an illustrative transseptal puncture device according to the invention.

FIGS. 20a-20d are overall side views of the blunt end cannula assembly with necked down distal portion of the improved embodiments. FIG. 20a is a side plan view of the assembly with the distal insert showing the blunt end of the cannula in FIG. 20e and the proximal inset showing the plan side view of the cannula valve and hub in FIG. 20b. A side cross sectional view of the hub and assembly is depicted in FIG. 20c with the proximal inset showing the hub with the valve in the open configuration in FIG. 20d.

FIG. 21a is a side plan view of the assembly with the distal insert showing the blunt end of the cannula in FIG. 21e and the proximal inset showing the plan side view of the valve and hub in FIG. 21b. A side cross sectional view of the hub and assembly is depicted in FIG. 21c with the proximal inset showing the hub with the valve in the open configuration in FIG. 21d.

FIG. 26 shows the curved introducer assembly in the configuration of FIG. 22 within the atrium of the heart with the blunt end dilator at or near a lower point on the septal wall distant from the target location at which septal penetration is desired.

FIG. 27 shows the introducer assembly of FIG. 26 in which the cannula carrying the guidewire has been advanced until the distal end of the cannula meets the internal distal stop in the blunt end dilator, showing how the cannula gives a predetermined desired shape to the introducer assembly to bring the blunt end dilator to the desired position on the septal wall where penetration is desired.

FIG. 28 is a side cross sectional view of the introducer assembly of FIG. 24 showing the blunt end dilator extending from the end of the introducer sheath and the cannula and guidewire disposed in the dilator in a more proximal position in the embodiment where the cannula has a stepped-down outer diameter which will allow it to extend past the internal distal stop in the blunt end dilator.

FIG. 29 shows the introducer assembly of FIG. 28 in which the stepped-down cannula carrying the guidewire has been advanced through the internal distal stop in the blunt end dilator, showing how the cannula gives a predetermined desired shape to the introducer assembly to bring the blunt end cannula to the desired position on the septal wall where penetration is desired.

FIG. 30 shows the curved introducer assembly of FIG. 27 in the desired position on the septal wall with the sharp tip guide wire advanced from the distal end of the blunt end dilator, across and through the septal wall into the opposing chamber in the heart. The guidewire has a distal curvature that bends back on itself to present a nontraumatic shape.

FIG. 31 shows the curved introducer assembly of FIG. 29 in the desired position on the septal wall with the sharp tip guide wire advanced from the distal end of the blunt end dilator, across and through the septal wall into the opposing chamber in the heart. The guidewire has a distal curvature that bends back on itself to present a nontraumatic shape. The stepped-down cannula has been advanced to the distal end of the blunt end dilator, but not beyond its distal tip.

FIG. 32 is a side cross sectional view of the introducer assembly of FIG. 30 after the blunt end dilator and introducer have been advanced over the guidewire through the septal wall and into the opposing heart chamber.

FIG. 33 is a side cross sectional view of the introducer assembly of FIG. 31 after the blunt end cannula has been advanced over the guidewire through the septal wall and into the opposing heart chamber. The introducer is not at this point yet advanced through the septal wall.

FIG. 34 is a side cross sectional view of the introducer assembly of FIG. 33 after the blunt end cannula, blunt end dilator and introducer have been advanced over the guidewire through the septal wall and into the opposing heart chamber.

DETAILED DESCRIPTION OF THE INVENTION

The invention described herein relates to devices and methods for puncturing the atrial septum via the percutaneous route for access to the left atrium through the right atrium for diagnostic or therapeutic purposes.

Devices and methods for performing a transseptal puncture procedure using a device which includes either an untapered or tapered blunt end cannula disposed in an introducer carrying a sharp guidewire disposed longitudinally through the lumen of the blunt cannula, wherein the guidewire is flexible and has an atraumatic conformation at its tip. The cannula gives the more flexible introducer a defined shape and steerabilty allowing an ordinarily skilled physician to easily access a selected location on the septal wall of the heart for transseptal puncture and introducer placement thereacross without employing an exposed sharp end needle or cannula during the procedure.

Figure 1:
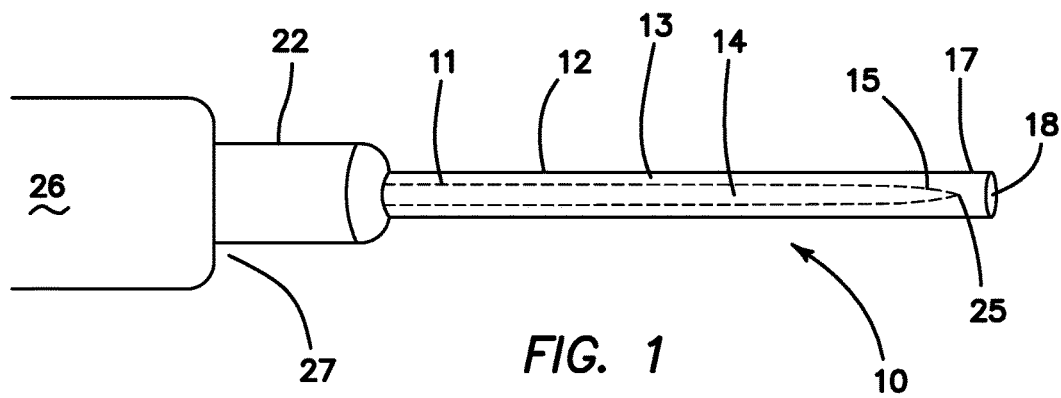
FIG. 1 is a plan view of a transseptal puncture device according to an illustrative embodiment of the invention.

In one aspect, the invention relates to a percutaneous device for making a transseptal puncture in the atrial septum of the heart. FIG. 1 is a plan view of the transseptal puncture device according to an illustrative embodiment of the invention. The illustrative percutaneous device 10 includes a blunt dilator 12 including a lumen 13 axially disposed along the long axis of the blunt dilator 12 and including a blunt distal end 17 having an opening 18. A second, inner sharp-tipped guidewire 14 is axially disposed within the lumen of the blunt dilator 12. The blunt dilator 12 provides structural support for the inner guidewire 14 and also functions as a dilator for the hole created in the atrial wall by the inner guidewire 14. The device 10 may further feature a transcutaneous intravascular sheath 22 through which the device 10 passes from outside the patient's body through a vessel, for example, the femoral vein, through the inferior vena cava to the right atrium, and a control handle 26 at the distal end 27 of the sheath 22. The sheath and/or other components of the delivery system may be steerable by actuators (not shown) on the control handle 26 to aid in delivering the device along the tortuous vascular path leading to the patient's right atrium. In certain embodiments, the distal end 17 of the blunt dilator 12 is tapered toward the inner guidewire 14, and the distal end 27 of the sheath 22 is tapered toward the blunt dilator 12.

In an embodiment, the blunt dilator 12 is similar in size to a transseptal dilator, e.g., with an inner tip diameter of about 0.8 mm. The percutaneous device 10 also features a septal perforator, for example, an inner guidewire 14. Alternatively, the septal perforator is a radio frequency electrode (not shown) that is coupled to the blunt dilator 12, or is a high pressure jet spray (not shown) that is emitted from the opening 18 of the blunt dilator 12.

Figure 2:
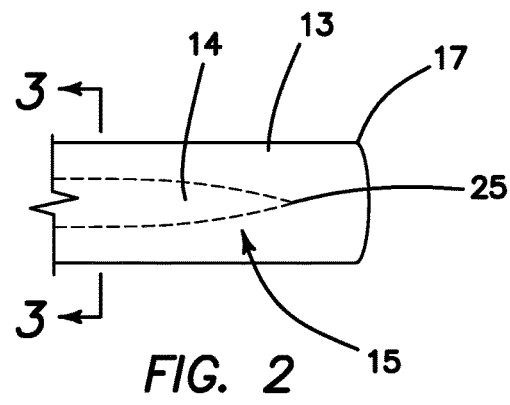
FIG. 2 is a longitudinal plan view of the distal end of a transseptal puncture device according to an illustrative embodiment of the invention.
Figure 3:
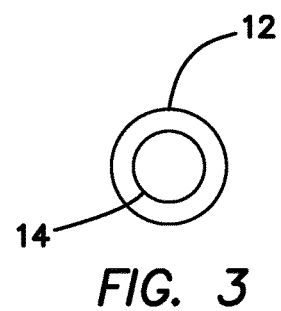
FIG. 3 is a cross sectional view of the distal end of a transseptal puncture device taken along lines 3-3 in FIG. 2.

In an embodiment depicted in FIGS. 2 and 3, the inner guidewire 14 includes a sharp tip 25 at a distal end 15 of the inner guidewire 14. The inner guidewire 14 is axially disposed within the lumen 13 of the blunt dilator 12. The inner guidewire 14 is reciprocally and axially moveable in the lumen 13 of the blunt dilator 12. The inner guidewire 14 can be rotated as well. The distal end 15 of the inner guidewire 14 is extendable through the opening 18 at the distal end 17 of the blunt dilator 12. The inner diameter of the lumen 13 of the blunt dilator 12 typically approximates the outer diameter of the inner guidewire 14.

The blunt dilator 12 and the inner guidewire 14 are made from various metals such as, for example, nitinol, steel, or titanium, or alloys thereof or polymers such as polyimide, PEBAX, polyethylene, polytetrafluoroethylene (EPTFE), Fluorinated ethylene propylene (FEP), and polyurethane. In one embodiment, the inner guidewire 14 is solid to increase its sharpness. Alternatively the inner guidewire 14 is hollow. The use of the blunt dilator 12 for introducing the inner guidewire 14 into the patient's cardiac tissue is preferred. In another embodiment, a sheath that is made from material that provides sufficient support during the transseptal puncture procedure is used and the blunt dilator 12 may not be needed.

Figure 4A:
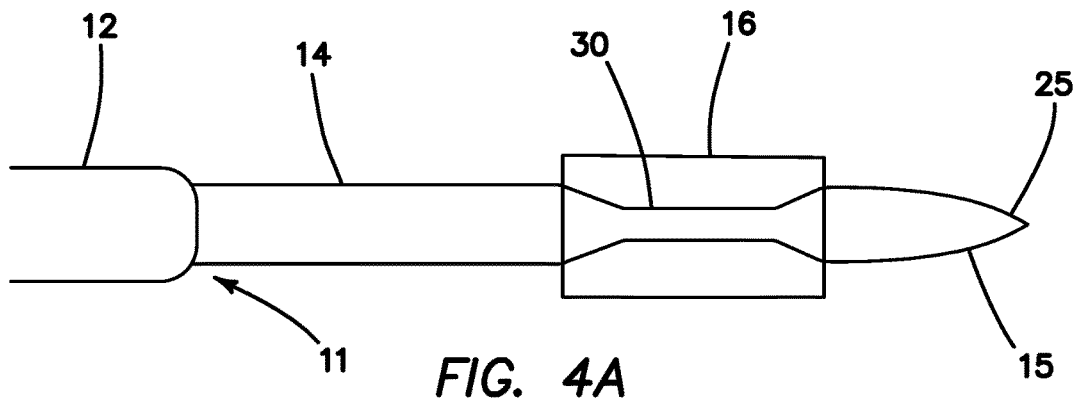
FIG. 4A is a longitudinal view of the distal end of a guidewire of a transseptal puncture device according to an illustrative embodiment of the invention in which the intermediate portion contains a waist.
Figure 4B:
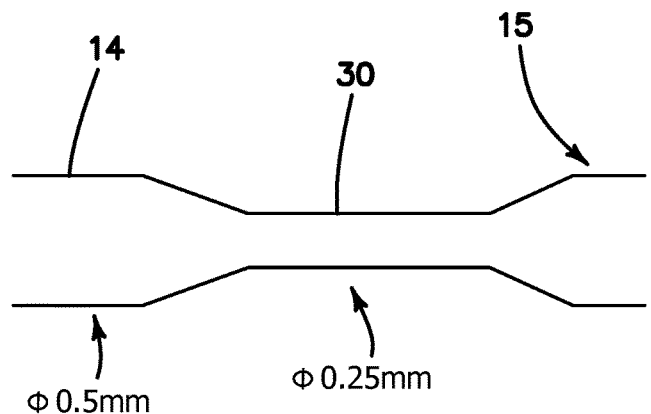
FIG. 4B is an exploded view of the intermediate portion of FIG. 4A.

FIGS. 4A and 4B are a longitudinal view and an exploded view, respectively, of the distal end of a guidewire of a transseptal puncture device according to another illustrative embodiment of the invention. The illustrative inner guidewire 14 includes a waist 30 near the distal end 15 of the inner guidewire 14. The waist 30 is positioned on an intermediate portion 16 of the inner guidewire 14 that is narrower in diameter than the portion of the inner guidewire 14 that is proximal to the intermediate portion 16 and the portion of the inner guidewire 14 that is distal to the intermediate portion 16. The waist 30 is thereby more flexible or bendable than the portions of the inner guidewire 14 that are proximal or distal to the waist 30. In one embodiment, the distal portion 15 is more flexible than the proximal portion 11 of the inner guidewire 14. The intermediate portion 16 having waist 30 is positioned about 5 mm to about 30 mm, preferably about 20 mm proximal to the distal end 15 of the inner guidewire 14. In an embodiment, the diameter of the waist 30 ranges from about 0.1 mm to about 0.5 mm, e.g., if the waist is composed of a metal, while the diameter of the inner guidewire 14 proximal to the waist 30 ranges from about 0.35 mm to about 1.5 mm and the diameter of the inner guidewire 14 distal to the waist 30 ranges from about 0.2 mm to about 1 mm. In another embodiment, the diameter of the waist 30 ranges from about 0.1 to about 1 mm, e.g., if the waist is composed of a non-metal, such as, for example, a polymer, such as (PEBAX) or polyurethane, a plastic, rubber, or any other polymer deemed suitable to those skilled in the art, or if the waist is comprised of a radiopaque coil, or a combination of non-metals, metal coils, with or without a solid metal core. In that case, the diameter of the inner guidewire 14 proximal to the waist 30 ranges from about 0.5 mm to about 3.0 mm and the diameter of the inner guidewire 14 distal to the waist 30 ranges from about 0.2 mm to about 3.0 mm. For example, the diameter of the waist 30 is about 0.2 mm, the diameter of the inner guidewire 14 proximal to the waist 30 is about 1 mm and the diameter of the inner guidewire 14 distal to the waist 30 is about 0.4 mm.

Figure 5:
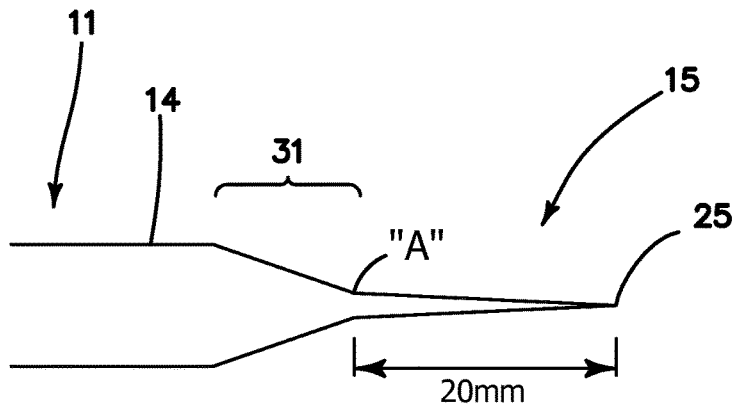
FIG. 5 is a longitudinal view of the distal end of a guidewire of a transseptal puncture device according to another illustrative embodiment of the invention in which the guidewire has a tapered intermediate portion.

FIG. 5 is a longitudinal view of the distal end of a guidewire of a transseptal puncture device according to another illustrative embodiment of the invention. In one embodiment, the inner guidewire 14 diameter is larger (e.g., 1 mm larger) at the proximal end of the inner guidewire 14 than the distal end 15. Alternatively, the inner guidewire 14 diameter is larger throughout the length of the inner guidewire 14 except for the most distal about 20 mm of the distal end 15. In one embodiment, the inner guidewire 14 contains a portion 31 at the distal end 15 that is tapered or the diameter of the inner guidewire 14 is gradually stepped down, for example, to a diameter of about 0.1 to about 0.25 mm, preferably about 0.2 mm, at a point "A" about 10 mm to about 20 mm proximal to the tip 25 of the guidewire 14. In an embodiment, the diameter of the guidewire 14 from the tip 25 to the point "A" is uniform. In a particular embodiment, the distal about 10 mm of the inner guidewire 14 adjacent to the tip 25 has a diameter of about 0.2 mm. According to this embodiment of the invention, the distal end 15 of the inner guidewire 14 is thinner and therefore is more flexible than the proximal portion 11 of the inner guidewire 14. In another embodiment the tapered or stepdown portion 31 can extend to the tip 25 of the inner guidewire 14 and can be about 5 mm to about 30 mm long.

Figure 6:
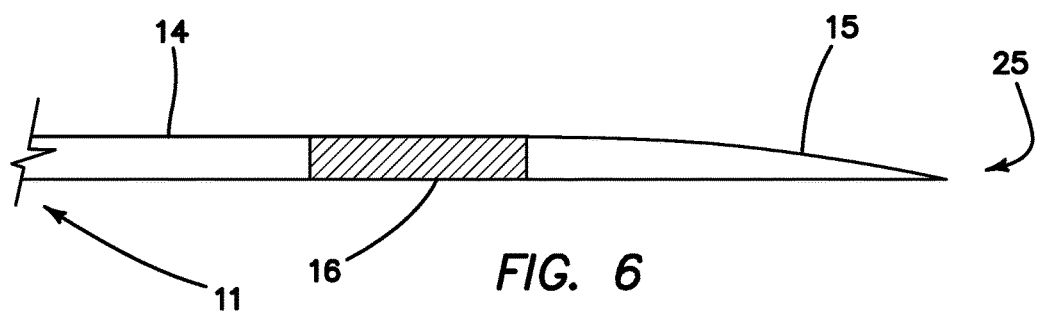
FIG. 6 is a longitudinal view of the distal end of a guidewire of a transseptal puncture device according to another illustrative embodiment of the invention, in which the guidewire has an intermediate portion.

FIG. 6 is a longitudinal view of the distal end of a guidewire of a transseptal puncture device according to another illustrative embodiment of the invention. At a position about 5 mm to about 30 mm, preferably about 20 mm from the distal end 15, the inner guidewire 14 includes an intermediate portion 16 manufactured from, or coated with, a material or treated such that the intermediate portion 16 is more likely to bend than the portions of the inner guidewire 14 that are proximal 11 and distal 15 to the intermediate portion 16. For example, if the inner guidewire 14 is composed of nitinol, the intermediate portion 16 may be annealed at 500 degrees Centigrade for 10 minutes to relieve stress in otherwise superelastic nitinol wire in an as-drawn condition. Alternatively, the intermediate portion 16 may be made from a softer or more flexible material than the proximal portion 11 and distal portion 15 of the inner guidewire 14. For example, the material of the intermediate portion 16 may be a polymer while the proximal portion 11 and distal portion 15 on the inner guidewire 14 are made from, for example, a rigid metal or, alternatively, a spring metal, polymer, or elastomer, a nickel titanium alloy or superelastic material such as nitinol. The intermediate portion 16 may be comprised of a coil, or a series of spaced bands, more specifically this coil or bands may be a radiopaque material such as gold, platinum, tungsten, iridium, palladium, or any other material easily visible with x-ray, ultrasound, MRI, or other imaging technique. The intermediate portion 16 may be welded to, crimped or attached by adhesives to the proximal portion 11 and distal portion 15 of the inner guidewire 14. In one embodiment, the intermediate portion 16 is about 0.5 mm to about 30 mm, preferably about 2 mm in length. Alternatively, geometric modification may make the intermediate portion 16 more flexible, for example, by the introduction of slits, grooves, cut-aways, notches, dimples, or other modification that thins portions of the wall of the intermediate portion 16.

In another embodiment (not shown), the distal, the proximal, and/or the intermediate portion (if present) of the inner guidewire 14 is flexible.

Figure 7:
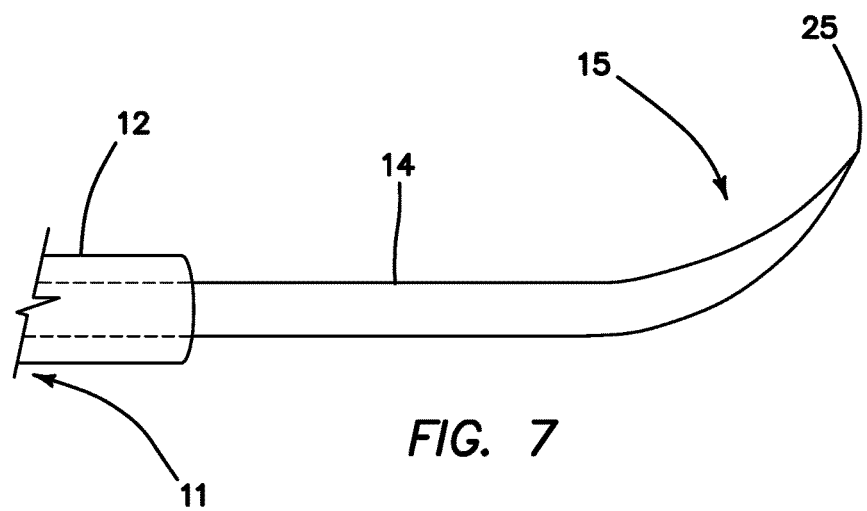
FIG. 7 is a longitudinal view of the distal end of a guidewire of a transseptal puncture device according to another illustrative embodiment of the invention in which the distal tip of the guidewire is bent.

FIG. 7 is a longitudinal view of the distal end of a guidewire of a transseptal puncture device according to another illustrative embodiment of the invention. The distal end 15 of the illustrative inner guidewire 14 may be straight (e.g., 0 degrees) or is bent at an angle ranging from about >0 degrees to about 270 degrees, preferably about 180 degrees relative to the long axis of the inner guidewire 14.

Figure 8:
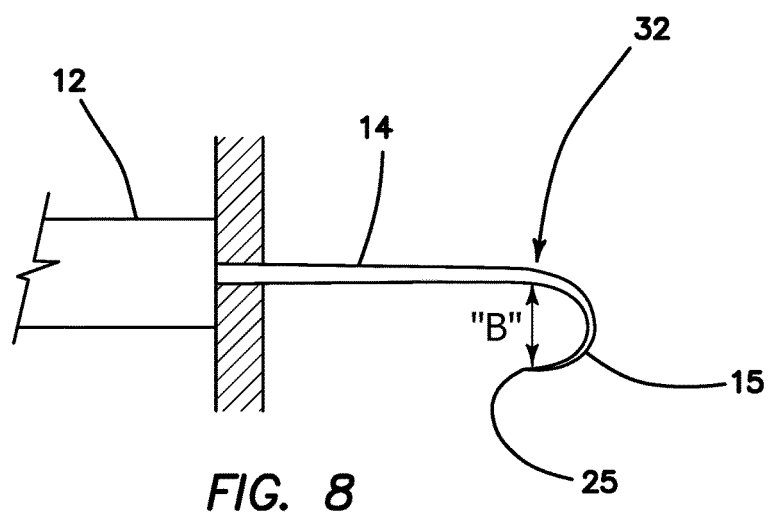
FIG. 8 is a longitudinal view of the distal end of a guidewire of a transseptal puncture device according to another illustrative embodiment of the invention in which the distal end of the guidewire has a hook.

Alternatively, referring to FIG. 8, when the distal end 15 of the inner guidewire 14 is not constrained within the lumen 13 of the blunt dilator 12, the distal end 15 has an essentially non-traumatic conformation, such as a helical, curved, cork screw, or hook shape. For example, the diameter "B" of the loop that forms the hook 32 can be between about 5 mm and about 30 mm, preferably about 10 mm. When the distal end 15 is enclosed within the lumen 13 of the blunt dilator 12, the entire length of the inner guidewire 14 is substantially straight and parallels the long axis of the blunt dilator 12.

In an alternative embodiment of the transseptal puncture device, the guidewire is replaced by a pulsating high pressure saline jet (or other suitable fluid) (not shown) generated by a pump. The jet spray is directed to the atrial septum from the distal end of the blunt, cannula according to the invention and incises the tissue. The cannula is then gradually advanced through the incision. Because the incision is made gradually and slowly, the method is safer than the currently used methods, for example, because there is a reduced risk of trauma and/or bleeding.

In yet another embodiment of the transseptal puncture device, the blunt, dilator is replaced by a radio frequency (RF) apparatus (not shown). The cannula according to the invention is insulated except for the dilator tip. The alternating current travels down the dilator. Preferably, unipolar electrodes can be used for the dilator with grounding pads typically placed on the patient's thighs. Alternatively, a bipolar electrode system can be employed as well. The application of RF to the dilator increases the tissue temperature around the dilator tip to over 100 degrees C. Mechanical cohesion in the tissue is diminished and allows the dilator to be advanced as pressure is applied to the tissue by the dilator tip. Any other method producing heat (e.g., such as electrical resistance, laser, or ultrasound) can be potentially used instead of RF. As with the saline jet described above, the incision is created slowly therefore the risk of accidental puncture of tissue that is not targeted for incision is minimal.

Figure 9D:
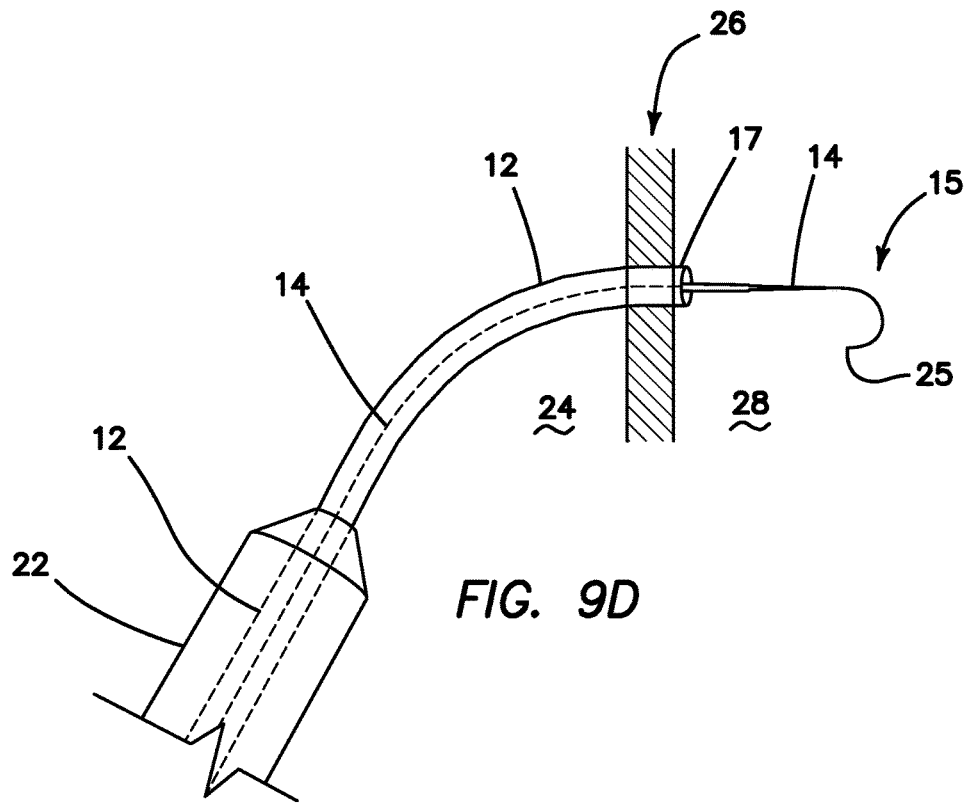

In another aspect, the invention provides a method using a percutaneous approach for puncturing the atrial septum of a patient to treat, for example, patent foramen ovale or to gain access to the left atrium to ablate the left atrial appendage. FIGS. 9A-9E depict the steps of an illustrative method for puncturing an atrial septum with the transseptal puncture device according to the invention. The illustrative method includes the step of introducing an intravascular sheath 22 in a vessel to access the lumen of the right atrium 24. In an embodiment, the sheath 22 is tapered to enhance advancement of the sheath 22 though the atrial septum 26. Referring to FIG. 9A, after the sheath 22 is properly positioned in the right atrium 24, the blunt dilator 12 of the transseptal device 10 is advanced distally toward the atrial septum 26 and positioned against septum primum 26a at the puncture site. The blunt distal end 17 of the blunt dilator 12 is then pushed against septum primum 26a until some tenting of the atrial septum 26 is visible. The tenting should be sufficient to correctly identify the puncture site in the septum primum 26a. Alternatively, visualization techniques such as, three-dimensional echocardiogram, ultrasound, or magnetic resonance imaging can be used that may work without tenting. Some amount of tenting also assists with the puncture itself.

Referring to FIG. 9B, once the blunt dilator 12 is positioned, the inner guidewire 14 is advanced relative to the blunt dilator 12 through the septum 26. At its most distal position, about 10 mm of the inner guidewire 14 should extend from the distal end 17 of the blunt dilator 12. Alternatively, the most distal position could be about 30 mm, if the distal portion 15 of the guidewire 14 had a hook shape, as is shown in FIG. 8. In an embodiment, the transition from the hook portion to the straight portion of the inner guidewire 14 is exposed. The blunt dilator 12 follows the path of the inner guidewire 14 to the septum 26. Because of the fine diameter, extreme sharpness, and the added stiffness provided by the blunt dilator 12, the inner guidewire 14 can be initially advanced into the septum 26. The motion of the inner guidewire 14 may be forward, vibrating, reciprocating, linear, or rotational, for example. In one embodiment, movement of the inner guidewire 14 is accomplished manually. Alternatively, movement of the inner guidewire 14 may be automated and therefore require additional controls such as a robotically actuated guidewire to be attached to the delivery system components such as the sheath 22. Such devices of the invention are easier for the doctor to manipulate and safer for the patient.

Figure 9E:
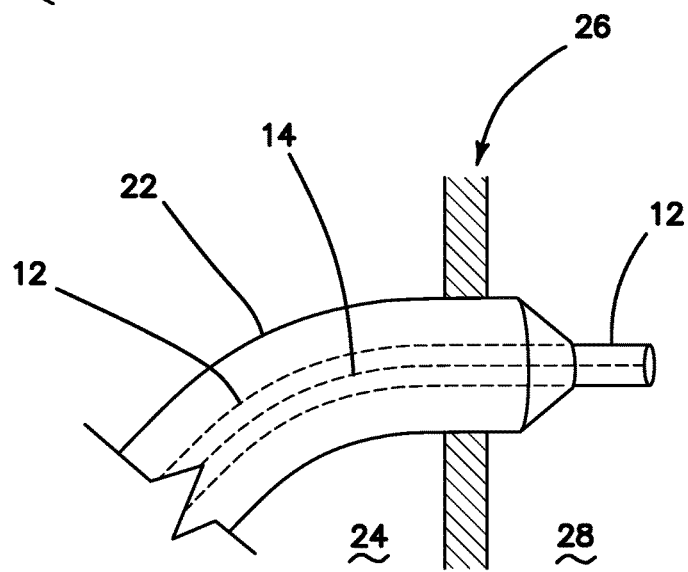
Figure 9F:
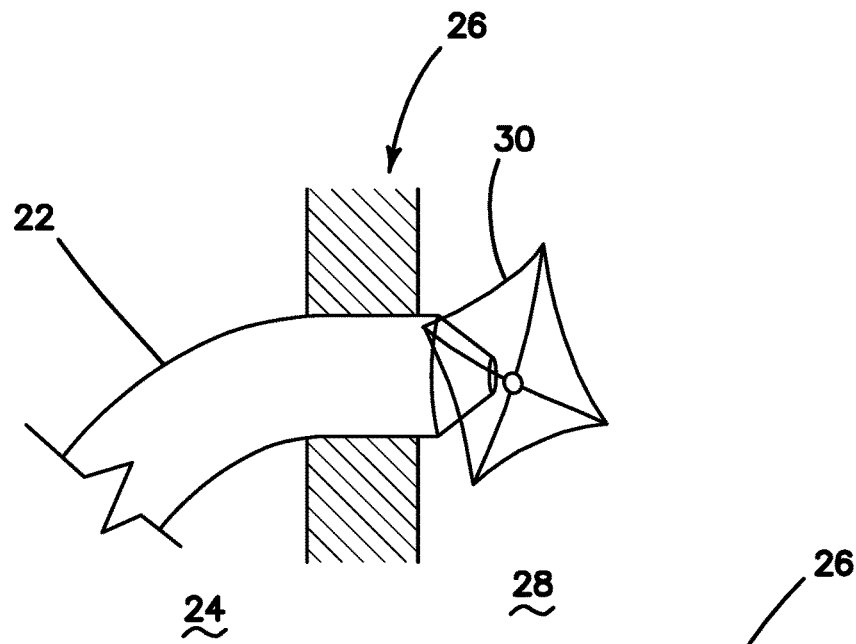
Figure 9G:
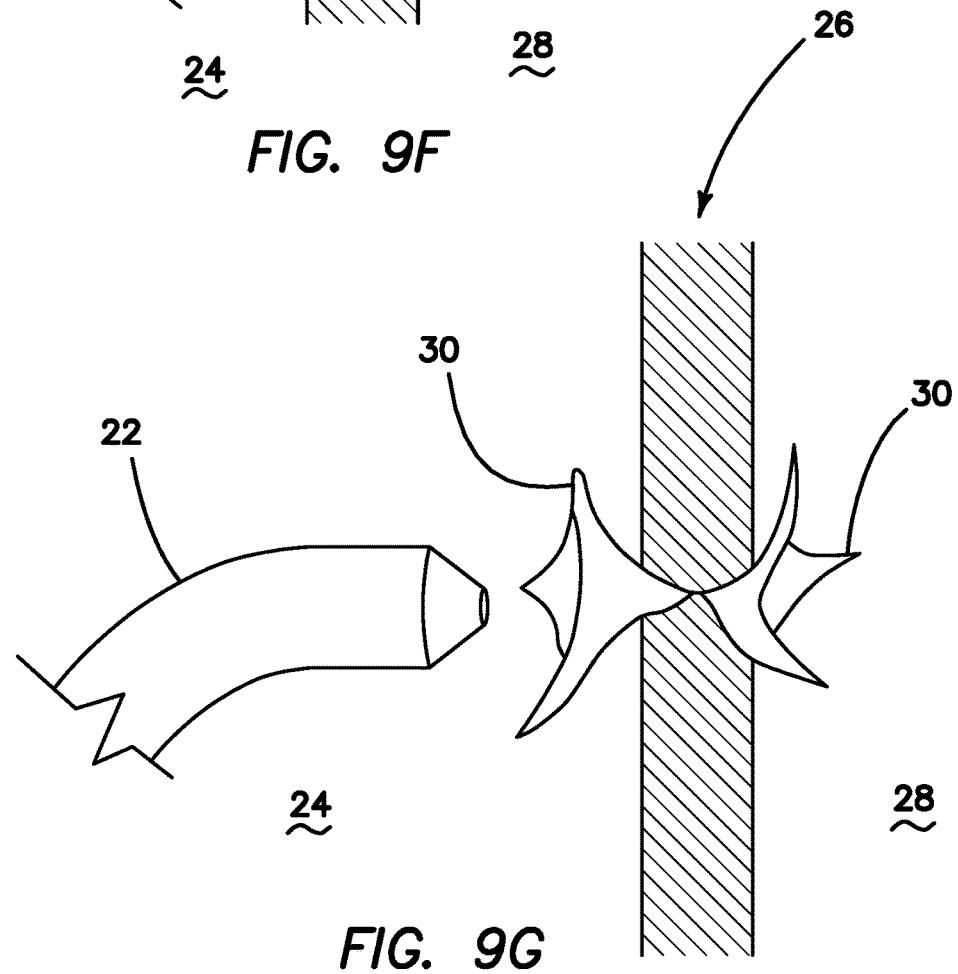

Referring now to FIG. 9C, once the distal end 15 of the inner guidewire 14 is positioned within the septum 26, the tissue provides support to the exposed part of the inner guidewire 14 until the whole tip of the inner guidewire 14 is delivered into the left atrium 28. The guidewire 14 may be advanced approximately 10 cm to sufficiently see the guidewire 14 outside of the cardiac silhouette, typically within the pulmonary veins using x-ray imaging or other imaging techniques. Referring to FIG. 9D, the blunt dilator 12 is advanced and positioned in the left atrium 28. Referring to FIG. 9E, standard catheterization laboratory procedures are utilized to place the sheath 22 within the left atrium 28. Once the sheath 22 is in the left atrium 28, the other components of the device, for example, the inner guidewire 14 and the blunt dilator 12, can be completely removed from the sheath 22 and the sheath 22 can be used to deliver implants, for example, such as an atrial occluder for the treatment of a patent foramen ovale, sutures, or other intracardiac therapeutic devices. For example, referring to FIG. 9F, one half of an occluder 30 is released from the sheath 22 and positioned in the left atrium 28. Referring to FIG. 9G, the sheath 22 is then withdrawn into the right atrium 24 and the other half of the occluder 30 is released and positioned in the right atrium 24. In an embodiment, the inner guidewire 14 is left behind, traversing the puncture site, and acts to maintain the puncture site as well as to act as a guidewire (e.g., and the blunt dilator 12 is withdrawn). In another embodiment, the inner guidewire 14 is withdrawn, e.g., into the blunt dilator 12.

The method for transseptal puncture using the transseptal device described herein is advantageous over conventional methods. For example, when using the devices and methods of the invention inadvertent contact of the inner guidewire 14 with the left atrial free wall (not shown) immediately after the septum 26 is punctured does not result in damage to or perforation of the left atrial free wall because the distal end 15 of the inner guidewire 14 is very flexible, as illustrated, for example, in FIG. 4 and corresponding text, or has an alternative curved tip 25, as illustrated, for example, in FIG. 8 and corresponding text, when fully extended from the distal opening 18 of the blunt dilator 12. When the distal end 15 of the inner guidewire 14 contacts the left atrial free wall, the distal end 15 of the inner guidewire 14 harmlessly bends rather than perforates the left atrial free wall. In one embodiment, the distal end 15 of the inner guidewire 14 bends because of the enhanced flexibility of the inner guidewire 14 at the intermediate portion 16, as described above in connection with FIGS. 4-8, between the proximal portion 11 and distal portion 15 of the inner guidewire 14. In an embodiment, perforation of the left atrial wall is avoided by modifying the shape of the inner guidewire 14 to form, for example, a hook or a bend.

Another advantage of the transseptal puncture devices described herein is the ability of the device to puncture through thick septum such as septum secundum. The transseptal puncture devices according to the invention can be used for remote suturing of a PFO or other defects that may be accessed percutaneously.

The transseptal puncture device according to the invention can also be used with various atrial septal defect locators such as those described in U.S. Ser. No. 10/660,444. For example, the locator may stabilize (e.g., constrain) the motion of the septa during insertion of the inner guidewire. Generally, a locator system includes a plurality of flexible members, at least one flexible member positionable on a side of the tissue opposite to another flexible member.

Figure 10:
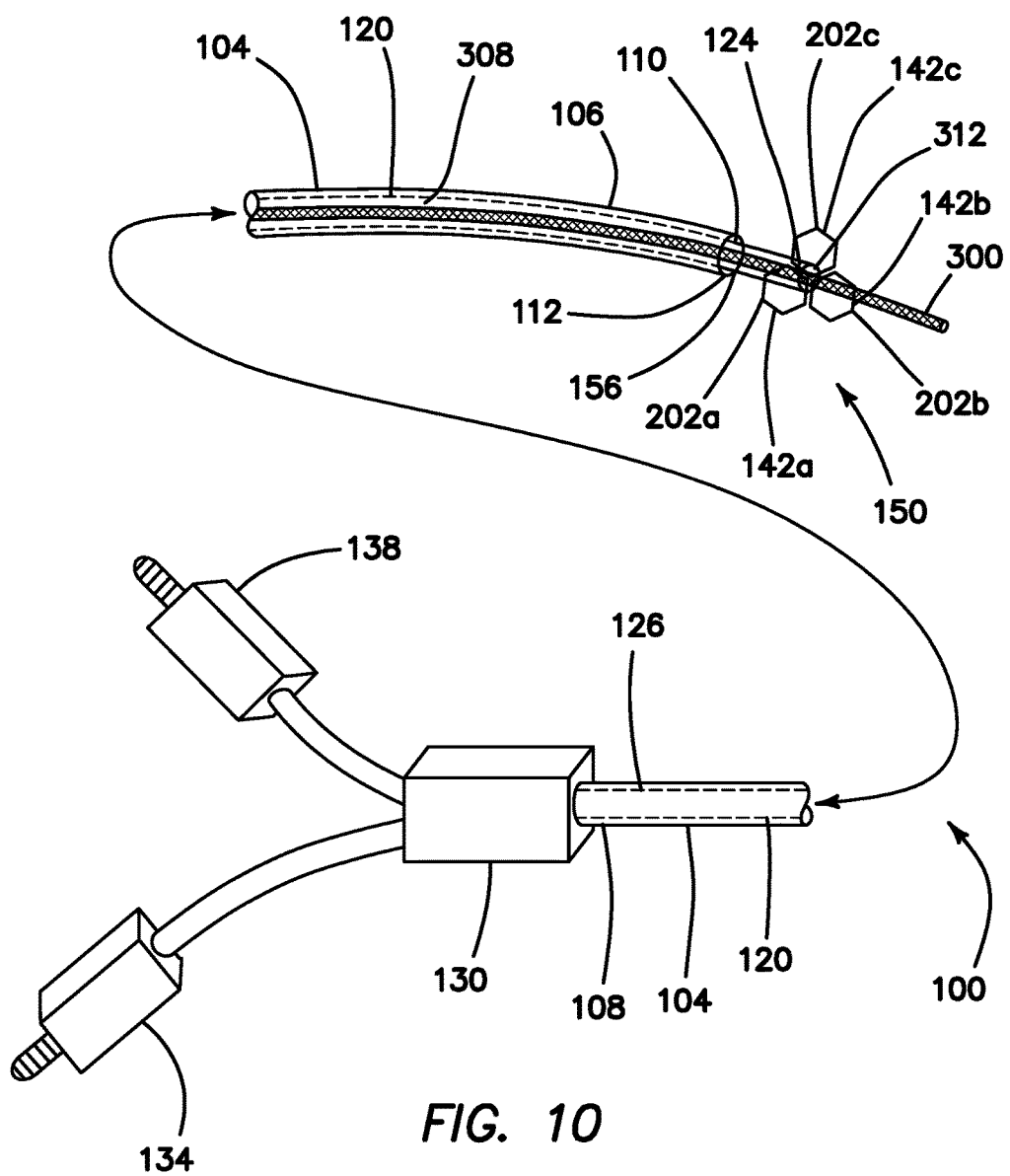
FIG. 10 is a fragmented illustration of a septal puncture apparatus according to an illustrative embodiment of the invention.

FIG. 10 illustrates a septal puncture apparatus 100 including three flexible members 142a, 142b, and 142c (generally 142) coupled to a delivery member 120 for applying, e.g., a pressure or force to a region in a body by pushing, pulling, or restraining the tissue, thereby stabilizing the tissue. The flexible members 142a, 142b, and 142c may be hexagonal in shape and coupled to a distal end 124 of the delivery member 120, thereby forming, generally, a planar array 150. The delivery member 120 is slideably receivable within a lumen 110 of the elongate member 104. Instruments, e.g., the delivery member 120 and a cutting member 300 (e.g., a member that perforate the tissue, which can comprise, referring to FIG. 1, an inner guidewire 14 and/or an blunt dilator 12, for example), are slideably receivable in the lumen 110 of the elongate member 104. In this embodiment, the cutting member 300 is slideably receivable in a lumen 308 of the delivery member 120 and extends distally or withdraws proximally from an opening 312 at the distal end 124 of the delivery member 120.

FIG. 10 also illustrates an exemplary interface 130 that permits controllers, for example, a set of apparatus controllers 134 and 138 to communicate with the elongate member 104 and the delivery member 120, respectively. The exemplary controllers 134 and 138 extend, retract, or otherwise manipulate, e.g., the elongate member 104 and the delivery member 120, respectively. A single controller, could, alternatively, control all functions and operations of the tissue puncture apparatus 100 and the instruments disposed therein.

By way of example, the elongate member 104 and the delivery member 120 are flexible tubes fabricated from a biocompatible material, e.g., polyethylene, polyether-amide block co-polymer (PEBAX), polyurethane, or fluorinated ethylene propylene.

By way of example, the flexible members 142 are manufactured using nickel-titanium material, such as Nitinol™ (Nitinol Devices and Components, Freemont, Calif.), or other shape memory alloy materials. The nickel-titanium wire, when properly manufactured, exhibits elastic properties for the wire to be manipulated (e.g., bent) by an operator and then returned to, substantially, the same shape the wire possessed prior to it being manipulated.

Figure 11:
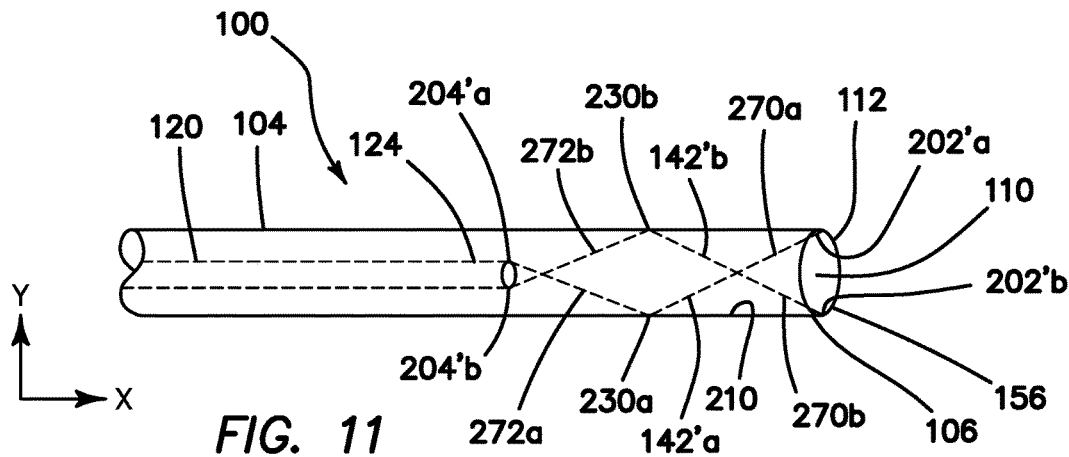
FIG. 11 is a schematic side view of a portion of a septal puncture apparatus including a set of flexible members according to an illustrative embodiment of the invention.

Alternatively, FIG. 11 illustrates a portion of a septal puncture apparatus 100 including exemplary flexible members 142'a and 142'b, which each include a leg such as a wire having a first end 204'a and 204'b, respectively, joined to the distal end 124 of the delivery member 120. Each of the flexible members 142'a and 142'b also have a second distal end 202'a and 202'b, respectively, that is free, i.e., not joined to any other structure of the septal puncture apparatus 100. The longitudinal axis of the flexible members 142'a and 142'b are oriented substantially parallel to the elongate member 104 when the flexible members 142'a and 142'b are located within the lumen 110 of the elongate member 104. The flexible members 142'a and 142'b have a first portion 272a and 272b, respectively and a second portion 270a and 270b, respectively. The flexible members 142'a and 142'b are disposed within the lumen 110 in a contracted position such that the second ends 202'a and 202'b are directed distally towards the opening 112 in the distal end 106 of the elongate member 104. The flexible members 142'a and 142'b are freed from the confines of the lumen 110 by moving the flexible members 142'a and 142'b between the contracted position illustrated, for example, in FIG. 11 and an extended position, such as the extended position depicted in FIG. 12B. After insertion into the lumen 110 of the elongate member 104, the flexible members 142'a and 142'b apply a force to an inner surface 210 of the elongate member 104 in a first location 230a and 230b, respectively, on the inner surface 210 of the lumen 110 that the flexible members 142'a and 142'b contact.

Figure 12A:
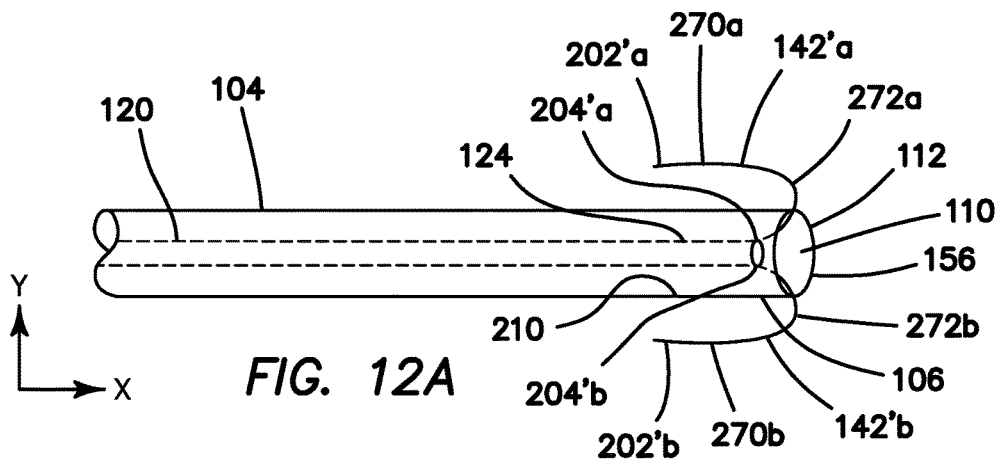
FIG. 12A is a schematic side view of a portion of an embodiment of a septal puncture apparatus including a set of flexible members partially extended from an elongate member.
Figure 12B:
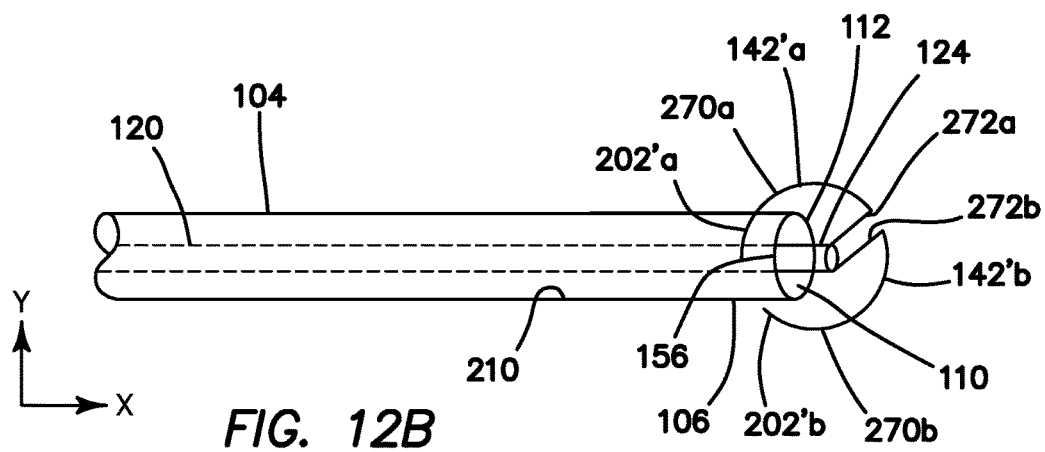
FIG. 12B is a schematic side view of the flexible members of FIG. 12A fully extended from the opening in the elongate member.

Referring now to FIG. 12A, as the delivery member 120 is extended out of the opening 112 of the elongate member 104, the second ends 202'a and 202'b of the flexible members 142'a and 142'b, respectively, undergo an articulation and point, generally, in a proximal direction toward the handle (not shown). Referring now to FIG. 12B, the elongated delivery member 120 is further extended distally along the lengthwise dimension (in the positive direction along the X-axis) of the lumen 110 until the distal end 124 of the delivery member 120 emerges from the opening 112 of the elongate member 104. The second ends 202'a and 202'b of the exemplary preshaped flexible members 142'a and 142'b, respectively, undergo an additional articulation and as a result point, generally, towards one another. In this extended position, each of the flexible members 142'a and 142'b is substantially planar in shape.

Alternatively, the second ends, for example, the second ends 202'a and 202'b, may have a different diameter than other locations along the length of the flexible elastic members 142'a and 142'b. By way of example, an operator may select an apparatus having flexible members that have second ends 202'a and 202'b having a larger diameter to, for example, reduce trauma to tissue the second ends 202'a and 202'b contact during use. Alternatively, the second ends 202'a and 202'b may have a ball shaped tip.

Figure 13:
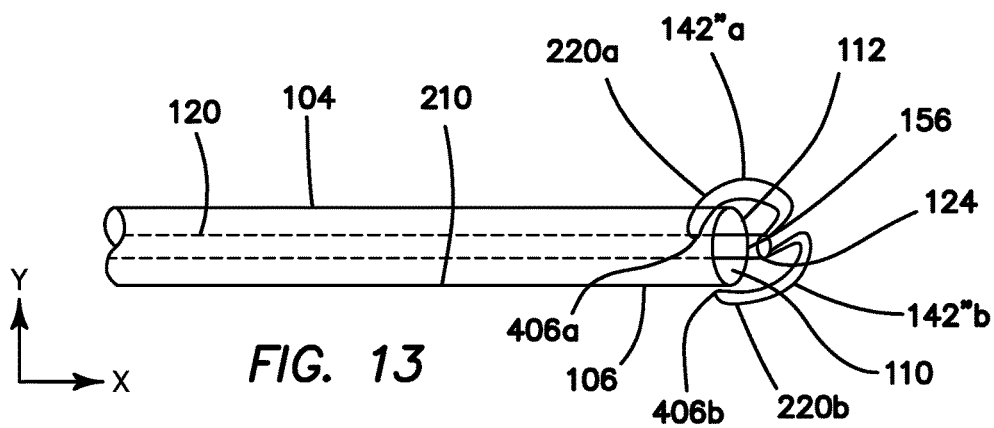
FIG. 13 is a schematic side view of another embodiment of a set of flexible members according to the invention.

FIG. 13 depicts exemplary flexible members 142"a and 142"b that include a first wire loop section 220a and a second loop section 220b, respectively. The tip 406a and 406b of the loop sections 220a and 220b, respectively, point, generally, towards one another and towards the delivery member 120. Loop sections 220a and 220b may, alternatively, be oriented in a variety of directions (e.g., away from the delivery member 120 or at a 45 degree angle away from the delivery member 120).

Figure 14A:
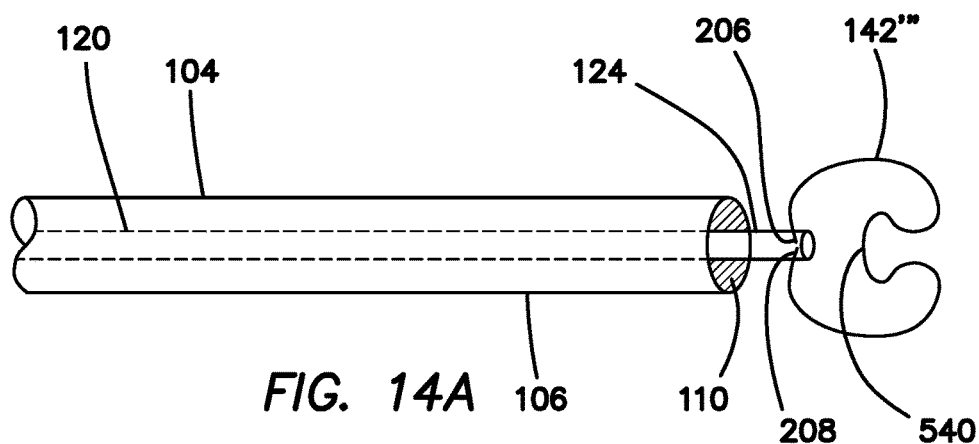
FIG. 14A is a schematic side view of an embodiment of a flexible member according to the invention.
Figure 14B:
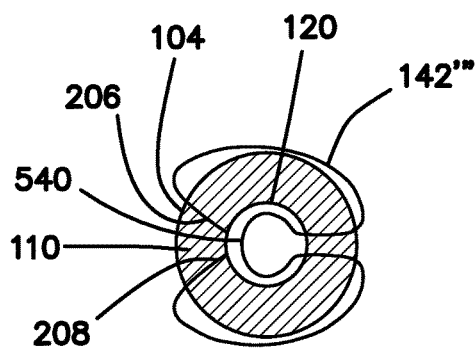
FIG. 14B is a schematic end-on view of the flexible member of FIG. 14A.

Referring now to FIGS. 14A and 14B, a septal puncture apparatus 100 includes a single flexible member 142''' that has a middle section 540 located, generally, intermediate the first end 206 and the second end 208 of the flexible member 142'''. The flexible member 142''' thereby forms a closed loop. In this embodiment, the flexible member 142''' is configured so the middle section 540 is located, generally in the center of a plane defined by the flexible member 142''' as illustrated by the end-on view of FIG. 14B. In this configuration, the middle section 540 of the flexible member 142''' aids with stiffening the flexible member 142''', which minimizes bending when, for example, the flexible member 142''' is used by an operator to apply forces to a tissue, e.g., the atrial septum. In this configuration, the flexible member 142 forms a closed loop that is sized and shaped, for example, to contact a first and second side of a tissue.

Figure 15B:
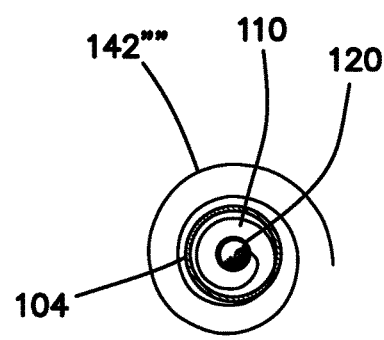
FIG. 15B is a schematic end-on view of the flexible member of FIG. 15A.
Figure 15A:
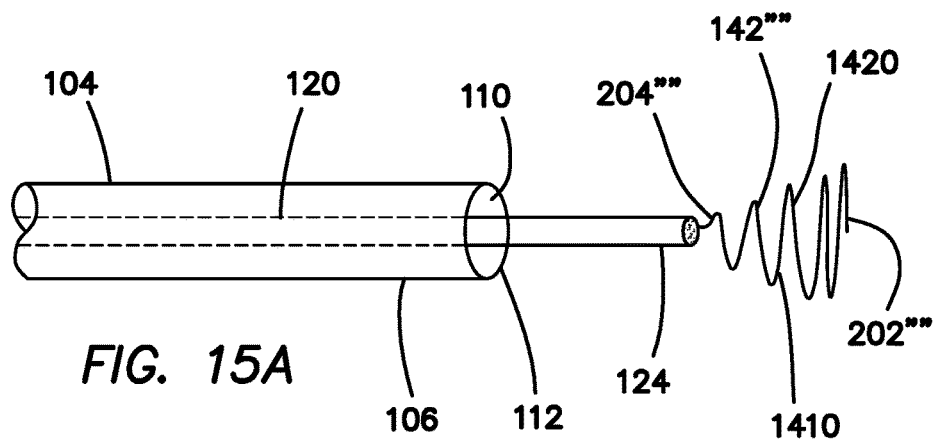
FIG. 15A is a schematic side view of an embodiment of a flexible member according to the invention.

Referring now to FIGS. 15A and 15B, the flexible elastic member 142'''' is a coil and has a spiral shape. By way of example, in use, a portion 1410 of the flexible member 142'''' can be located on a first side of a tissue and a portion 1420 of the flexible member 142'''' can be located on a second side of a tissue. For example, the flexible member 142'''' can be screwed through a tunnel or a hole, such as a defect in the atrial septum. Alternatively, the distal end 124 of the delivery member 120 may be located axially through, for example, a hole in a tissue such that the flexible member 142'''' may be withdrawn partially through the hole by a rotational (screw-like) motion of the delivery member 120 thereby locating the portion 1410 of the flexible member 142'''' on a first side of the tissue and the portion 1420 of the flexible member 142'''' on a second side of a tissue.

Figure 16A:
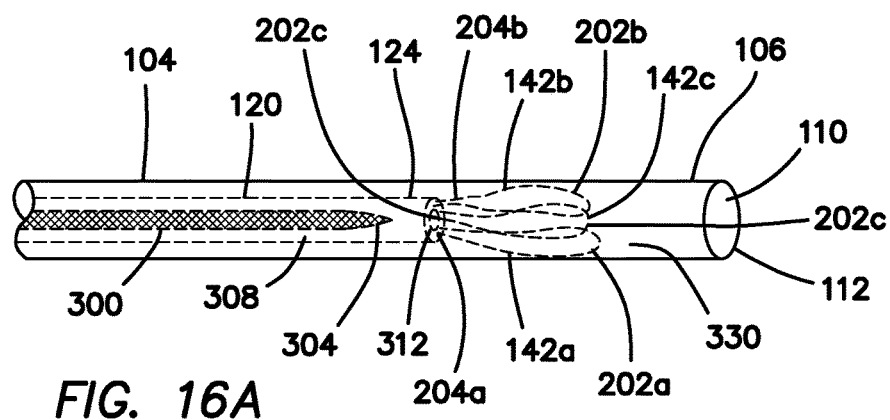
FIG. 16A is a schematic side view of an embodiment of a set of flexible members, a cutting member, and an elongate member of a portion of a septal puncture apparatus according to the invention.
Figure 16B:
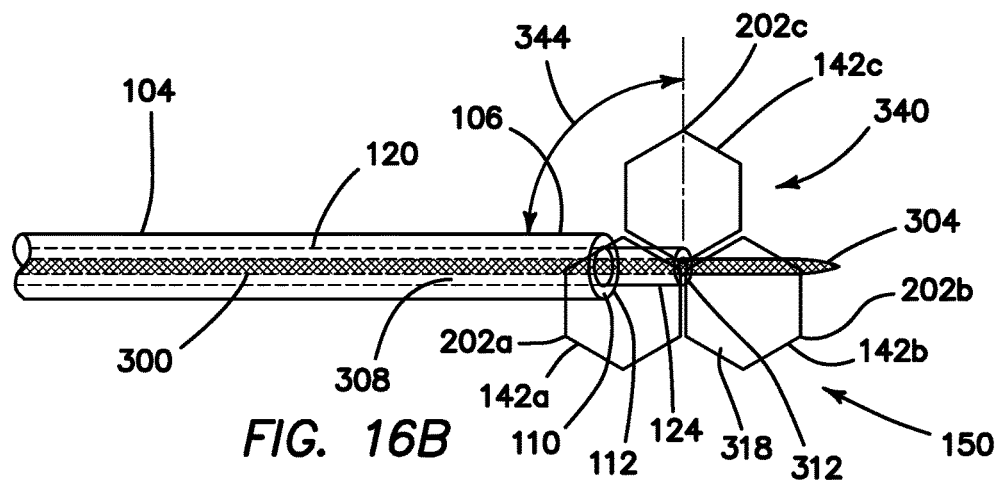
FIG. 16B is an illustration of the set of flexible members and the cutting member extended out of the elongate member of FIG. 16A.

Referring to FIG. 16A, the delivery member 120 is translated axially along the lengthwise dimension of the lumen 110 until the distal end 124 of the delivery member 120 emerges from an opening 112 in the elongate member 104 and the flexible members 142a, 142b, and 142c transition from the contracted first position 330 shown in FIG. 16A to a second extended position 340 shown in FIG. 16B. The exemplary flexible members 142a, 142b, and 142c expand to assume, for example, substantially hexagonal shapes upon emerging from the opening 112 in the elongate member 104 and expanding. The extended flexible members 142a, 142b, and 142c are substantially planar. The plane defines a plurality of axes that lie in the plane and the plurality of axes are non-parallel to (i.e., biased relative to) the elongate member 104. An angle 344 defined by at least one of the plurality of axes of the plane of the flexible members 142a, 142b, and 142c and the longitudinal axis of the elongate member 104 is typically specified (e.g., by an operator) such that the flexible members 142a, 142b, and 142c are flush with tissue surface and are capable of applying a force across a large tissue area. For example, the angle 344 might be chosen to ensure the flexible members 142a, 142b, and 142c conform to the shape of a tissue surface abutting the flexible members 142a, 142b, and 142c. If the force is applied, e.g., across a large tissue area the movement of the tissue in any location across the tissue area will be minimized. The flexible members 142a, 142b, and 142c could, alternatively, be of any shape (e.g., polygonal, circular, or ellipsoidal) or of any quantity (e.g., one, two, or five) where the shape and/or quantity of the flexible members 142a, 142b, and 142c are typically selected to distribute as much force as possible while still being able to fit within the lumen 110 of the elongate member 104 and emerge from or retract into the lumen 110.

When the flexible members 142a, 142b, 142c are extended in the second expanded position 340 upon emerging from the opening 112, the exemplary cutting member 300 extends axially in the lumen 308 of the delivery member 120 until a cutting tip 304 of the cutting member 300 emerges from the opening 312 in the distal end 124 of the delivery member 120. The tip 304 of the cutting member 300 cuts the tissue in close proximity to the opening 312 of the delivery member 120.

Figure 17:
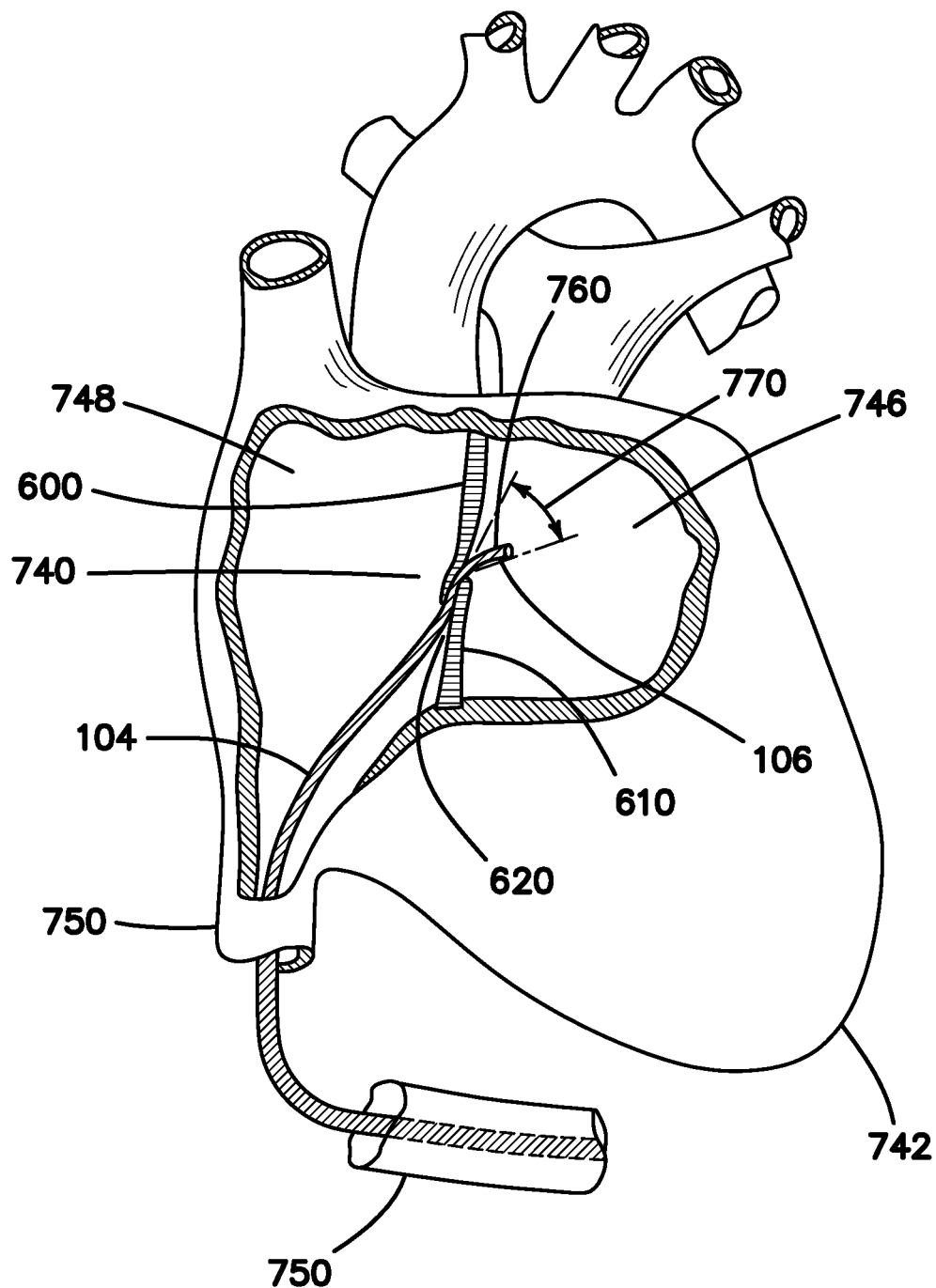
FIG. 17 is a partially broken-away view of a heart depicting a portion of a septal puncture apparatus, according to the invention, on a second side of the septal wall.

Referring now to FIG. 17, an operator introduces an elongate member 104 into the right atrium 748 of a heart 742 through the descending vena cava 750. The elongate member 104 is advanced distally until the distal end 106 of the elongate member 104 passes through a defect 620 (for example, a patent foramen ovale) in the septum 740. The distal end 106 of the elongate member 104 is shown at an angle 770 of about 45 degrees relative to the longitudinal axis of the elongate member 104 due to a bend 760 in the distal end of 106 of the elongate member 104. The bend 760 in the elongate member 104 may be mechanically pre-formed or pre-bent at the angle 770 between about 0 degrees and about 180 degrees prior to insertion of the elongate member into the body. The bend 760 could, alternatively, be accomplished by heating a nickel-titanium material or other shape memory alloy located within the distal end 106 of the elongate member 104.

Figure 18A:
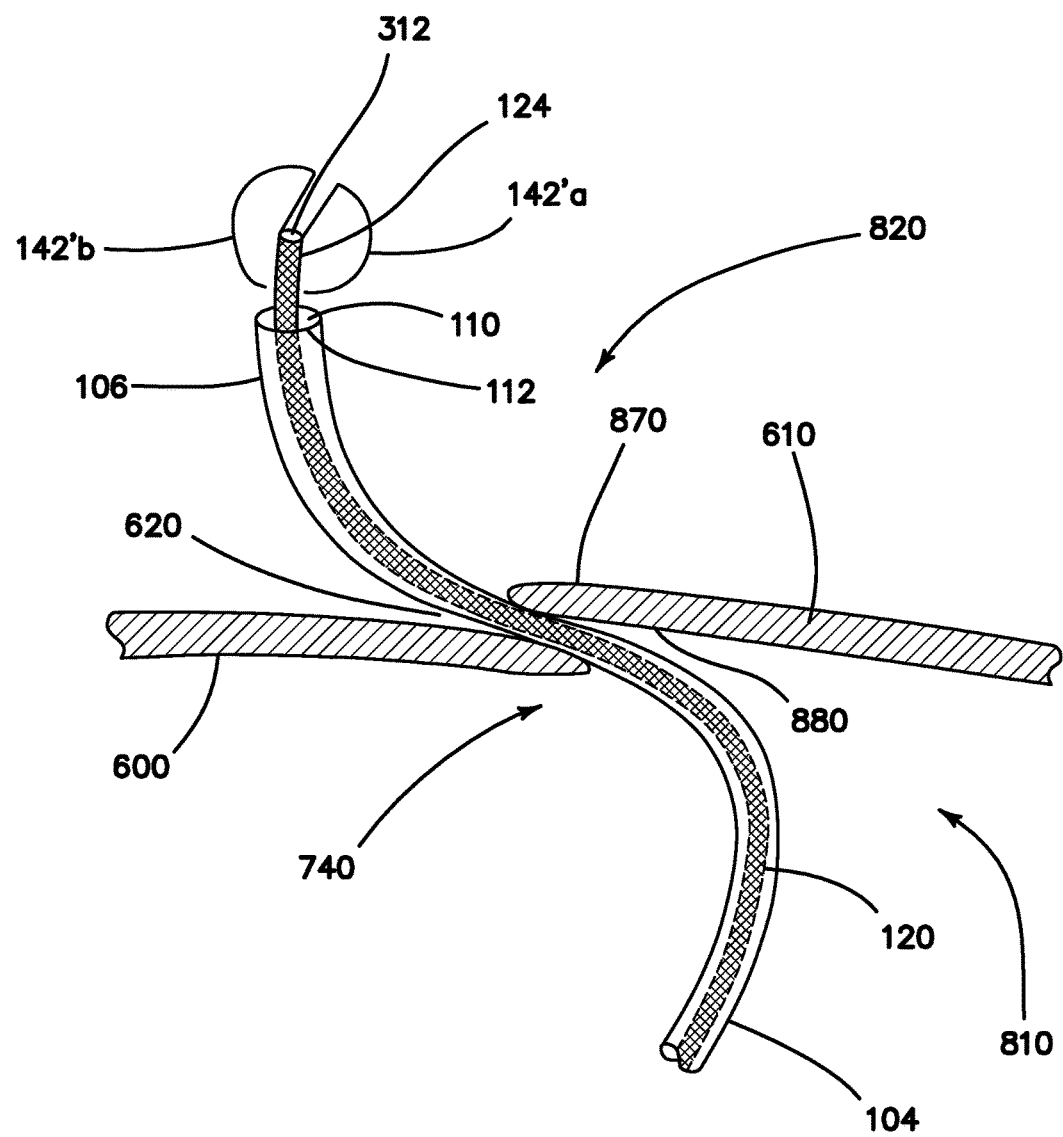
FIG. 18A is a cross-sectional view of a septal wall of a heart depicting a set of flexible members located outside an opening in an end of an elongate member, according to an illustrative embodiment of the invention.
Figure 18B:
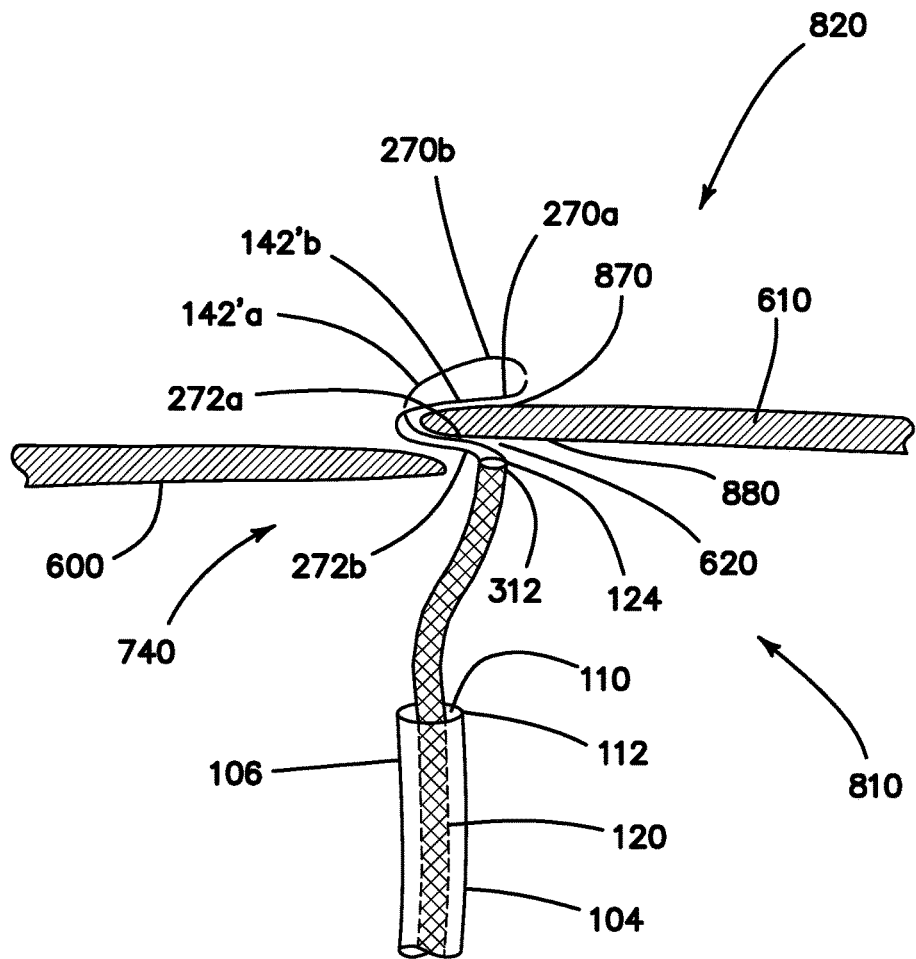
FIG. 18B is a cross-sectional view of the flexible members of FIG. 19A in which a portion of the flexible members is located in contact with a first side of a septal wall and another portion of the flexible members is located in proximity to a second side of the septal wall.
Figure 18C:
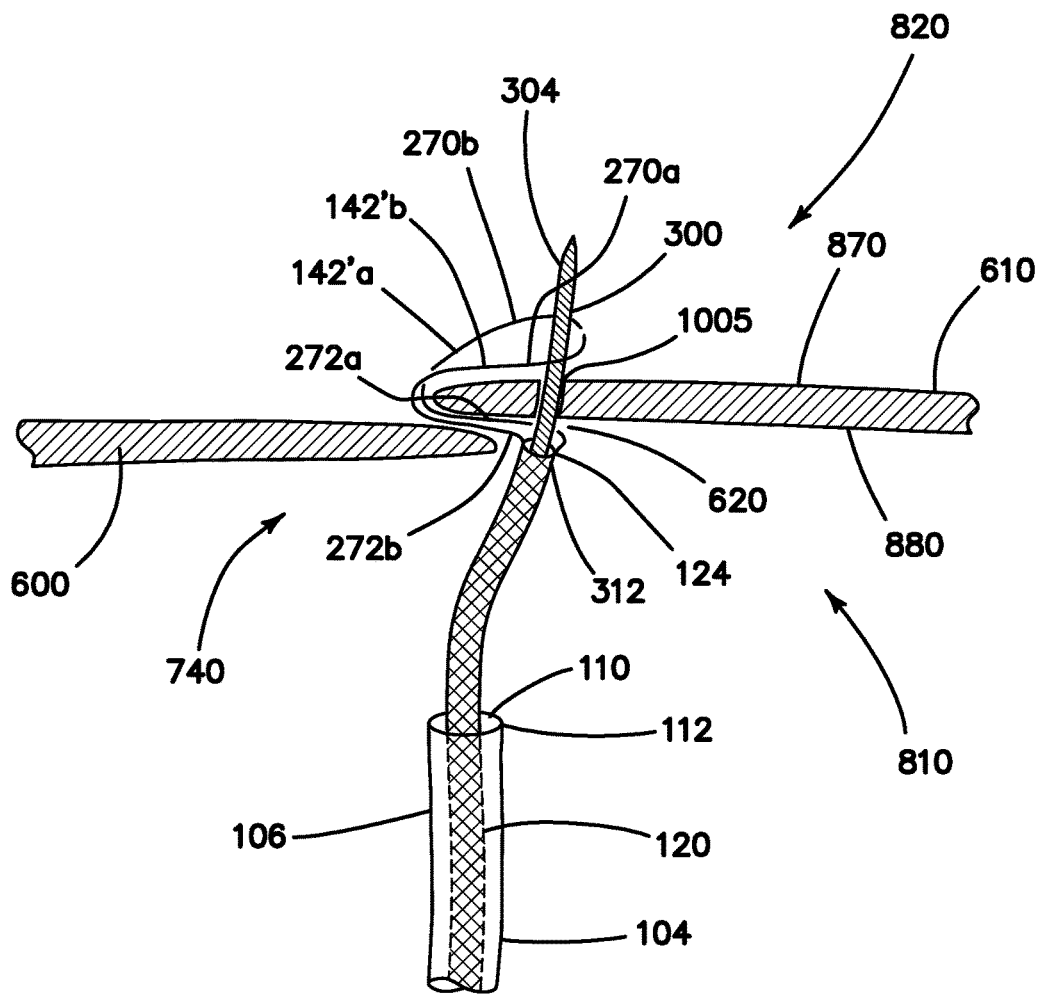
FIG. 18C is a cross-sectional view of the flexible members of FIGS. 19A and 19B in which a cutting member is extended from a lumen in the delivery member creating a hole through the septal wall.

The septal puncture apparatus shown in FIGS. 18A, 18B, and 18C includes two flexible members 142'a and 142'b coupled to the distal end 124 of the delivery member 120. The flexible members 142'a and 142'b are initially located within the lumen 110 of the elongate member 104. An operator initially guides the distal end of 106 of the elongate member 104 through the defect (hole) 620 such that the distal end 106 is located on a second side 820 (in the left atria of the heart) of the septum secundum 600 and septum primum 610. Now referring to FIG. 18A, the operator then extends the flexible members 142'a and 142'b as described herein with respect to, for example, FIGS. 12A and 12B.

With continued reference to FIG. 18A, the elongate member 104 is retracted proximally until the distal end 106 of the elongate member 104 passes back through the defect 620 and is positioned on the first side 810 of the septum 740.

The delivery member 120 is then retracted proximally so the second portions 270a and 270b of the flexible members 142'a and 142'b and the distal end 124 of the delivery member 120 are in close proximity to the defect 620, the septum primum 610, and the septum secundum 600 on the second side 820 of the septum 740.

Now referring to FIG. 18B, as the delivery member 120 is further retracted proximally such that the distal end 124 of the delivery member 120 is withdrawn through the defect 620 until it is in contact with or in close proximity to the first surface 880 of the septum primum 610 on the first side 810 of the septum primum 610. The second portions 270a and 270b of the flexible members 142'a and 142'b are positioned, generally non-parallel to the longitudinal axis of the elongate member 104 and are in physical contact with at least the second surface 870 of the septum primum 610 on the second side 820 of the septum primum 610 and also partially located within the defect 620 in the septum 740. The first portions 272a and 272b of the flexible members 142'a and 142'b are located on the first side 810 of the septum 740. Accordingly, the flexible members 142'a and 142'b are sized and shaped for contact with the first side 810 and the second side 820 of the septum 740. The flexible members 142'a and 142'b are thus capable of limiting movement of the septum primum 610. Now referring to FIG. 18C, the cutting member 300 is extended from the opening 312 in the distal end 124 of the delivery member 120. The cutting tip 304 of the cutting member 300 introduces a hole 1005 (tissue opening) through the septum primum 610.

Figure 19:
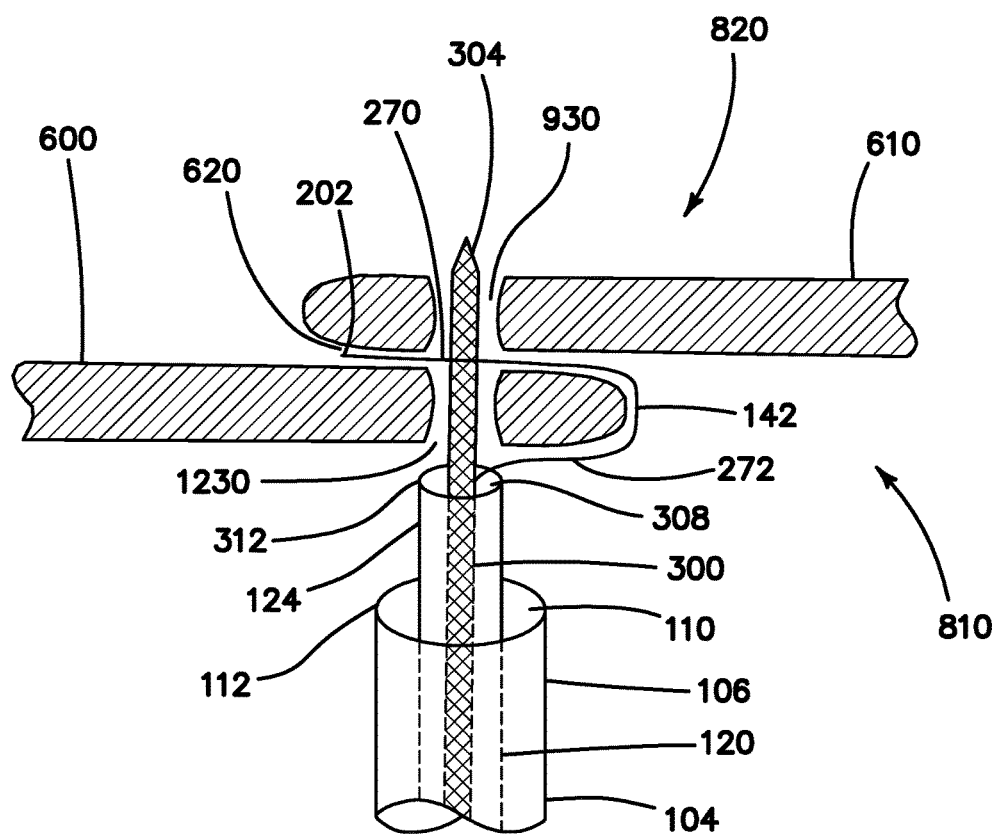
FIG. 19 is a schematic side view of a flexible member, a cutting member, and an elongate member according to an illustrative embodiment of the invention.

Referring now to FIG. 19, an exemplary flexible member 142 is attached to the distal end 124 of the delivery member 120, which extends from the opening 112 in the distal end 106 of the elongate member 104. The delivery member 120 and the elongate member 142 are located on the first side 810 of the septum secundum 600. The distal end 124 of the delivery member 120 is located in close proximity to the tissue surface of the septum secundum 600 on the first side 810 of the septum secundum 600. The flexible member 142 extends through the hole 620 between the septum primum 610 and the septum secundum 600 from the first side 810 to the second side 820. The first side 810 of the septum primum 610 opposes the second side 820 of the septum primum 610. The flexible member 142 is positioned so that the second end 202 and second portion 270 of the flexible member 142 are located on the second side 820 of the septum secundum 600 and the first portion 272 of the flexible member 142 is located on the first side 810 of the septum secundum 600. In this configuration, the flexible member 142 is thus capable of limiting movement of the septum secundum 600. In this embodiment only the septum secundum 600 is secured to limit movement. In alternative embodiments, however, the septum secundum 600 and/or the septum primum 610 may be secured to limit movement.

Figure 22:
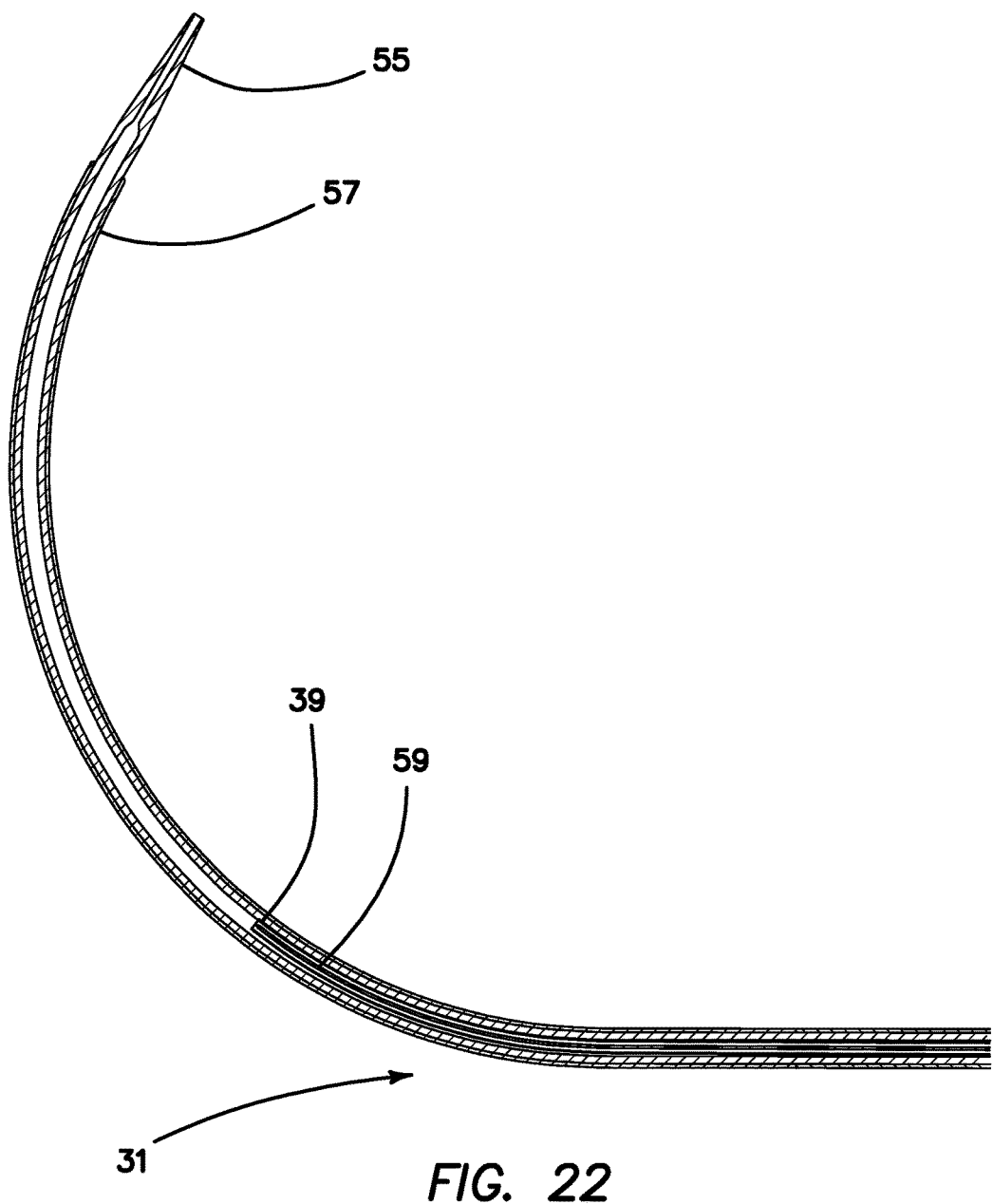
FIG. 22 is a side cross sectional view of the introducer assembly in enlarged scale showing the blunt end dilator extending from the end of the introducer sheath and the cannula and guidewire disposed in the dilator in a more proximal position.

Turning to FIGS. 20a-20d which show overall side views of the blunt end cannula assembly of the improved embodiments. FIG. 20a is a side plan view of the cannula assembly 34 with the distal insert 33 showing the blunt end 37 of the curve 40 in FIG. 20e and the proximal inset 75 showing the plan side view of the valve 41 and hub 43 in FIG. 20b. A side cross sectional view of the hub 43 and assembly 34 is depicted in FIG. 20c with the proximal inset 45 showing the hub 43 with the valve 41 in the open configuration in FIG. 20d. The cannula assembly 34 comprises a tubular cannula 35 that may be metal, polymer, composite, or glass, though preferably stainless steel or nickel titanium alloy. The distal end of the tubular cannula 35 is necked down, tapered, or formed from two pieces so that the distal diameter is able to fit through the smaller diameter of an introducer dilator 55 (FIG. 22). The proximal portion of the tubular cannula 35 is typically 18 gauge for adult sized systems and 19 gauge for pediatric systems, though may be as large as 12 gauge and as small as 30 gauge, whereas the distal necked down portion of the tubular cannula 35 is typically 21 gauge for adult sized systems and 22 gauge for pediatric systems, though may be as large as 15 gauge and as small as 36 gauge. The tubular cannula 35 inner diameter is a function of the cannula wall type which is typically regular wall (RW) or thin wall (TW) but may also be extra thin wall (ETW), ultrathin wall (UTW) or microthin wall (MTW) as provided by K-Tube Technologies in Poway, Calif. The inside surface finish of the tubular cannula 35 can be as low as 4 RMS (root mean square in micro-inches, which is a surface finish measurement based on the average of the peaks and valleys of the surface profile) to as high as 125 RMS, though preferably is fabricated by being plug drawn with a smoother <32 RMS to facilitate insertion of devices through the cannula. The distal curve 40 serves to steer the introducer assembly 31 (FIG. 22) to the desired anatomy of the heart. The curve radius is typically around 50 mm but my be as small as 25 mm and as large as 100 mm, with arclengths ranging from 10 mm to 100 mm but preferably between 35 to around 75 mm. Another aspect of the tubular cannula 35 is that it may be formable or malleable so that the end user can increase or decrease the amount of curve 40 depending on the specific anatomy of the patient. The proximal end of the tubular cannula 35 is coupled to a hub 43 such that rotation or motion of the hub 43 is precisely transmitted to the cannula 35, and steering of the curve 40 may be accomplished by the user through manipulation of the hub 43. Any suitable connection may be used between the cannula 35 and the hub 43, though a press fit and adhesive are preferred, other methods such as solder, welding, compression fit, screws, or flaring may also be used, and the connection may be releasable if a single hub 43 is used with different lengths of cannula 35. Typical lengths for the cannula 35 match the transseptal introducers currently available, and are 56 cm, 71 cm, 89 cm, 98 cm, and 101 cm, though it is conceived that any length suitable for reaching the heart from the groin, abdomen, or chest. The hub 43 may be made of metal, polymer, elastomer, composite, or ceramic, though it is most desirable to fabricate the hub from a polymer such as polycarbonate so that it can be transparent or translucent. A proximal Luer fitting on the hub 43 enables a fluid or pressure line to be releasably connected and be in fluid communication with the inner diameter of the tubular cannula 35. Also in fluid communication with the hub 43 is a valve 41 which enables the fluid communication to be open or closed in a similar fashion to a stopcock. The fluid communication as shown in FIG. 20d is a one way, on/off design, however it is also conceived to add additional ports to allow for additional devices and lines to be connected and be in fluid communication with the inner diameter of the tubular cannula 35. Additional valves may also be provided on these additional ports so as to control fluid, air, blood flow through these ports. The valve 41 may be made of metal, polymer, elastomer, rubber, composite, or ceramic, though it is most desirable to fabricate the hub from a polymer such as high density polyethylene so that when mated with hub 43, the valve 41, which also incorporates a handle shape, may provide a hemostatic fluid tight connection.

Figure 21A:
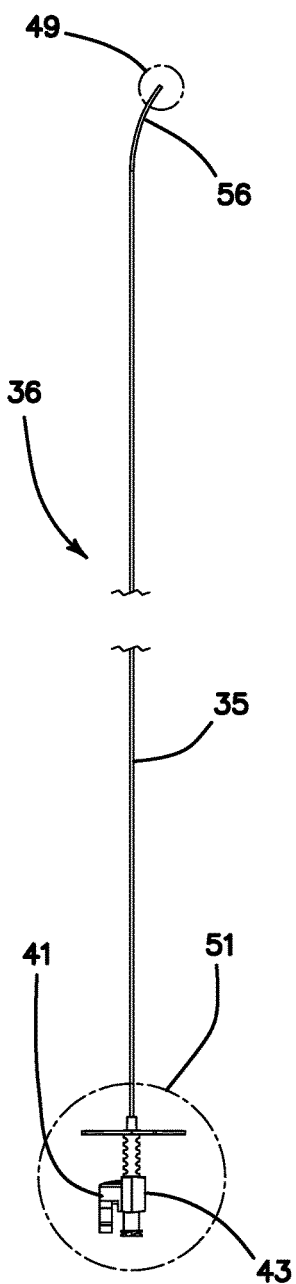
FIGS. 21a-21d are overall side views of the blunt end cannula assembly of the improved embodiments.
Figure 21B:
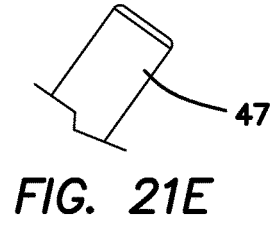
Figure 21C:
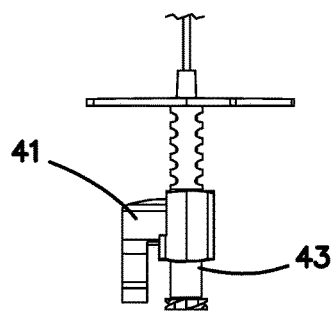
Figure 21D:
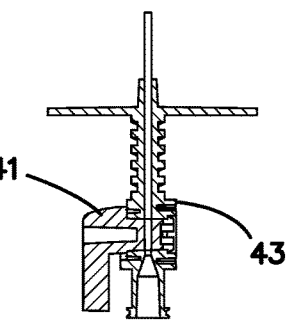
Figure 21E:
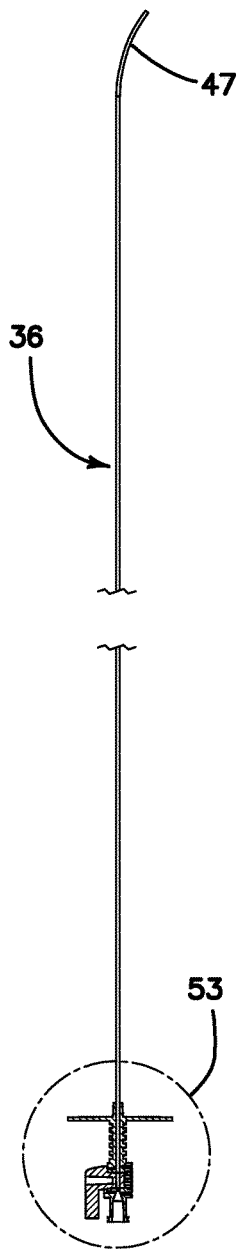

FIGS. 21a-21d are overall side views of the cannula assembly 36 of the improved embodiments. FIG. 21a is a side plan view of the assembly 36 with the distal insert 49 showing the blunt end 47 of the curve 56 in FIG. 21e and the proximal inset 51 showing the plan side view of the cannula valve and hub in FIG. 21b. A side cross sectional view of the hub 43 and assembly 36 is depicted in FIG. 21c with the proximal inset 53 showing the hub 43 with the valve 41 in the open configuration in FIG. 21d.

FIG. 22 is a side cross sectional view of the introducer assembly 31 in enlarged scale showing the blunt end dilator 55 extending from the end of the introducer sheath 57 and the cannula 39 and guidewire 59 disposed in the dilator 55 in a more proximal position. The untapered cannula 39 is used inside the introducer sheath 57 to shape the introducer assembly 31, provide it with enhanced steerability, and to provide columnar support for both the introducer assembly 31 and the floppy guidewire 59 allowing it to be pushed through the septum and thereafter assume an atraumatic J-shaped configuration as it is advanced further.

Figure 23:
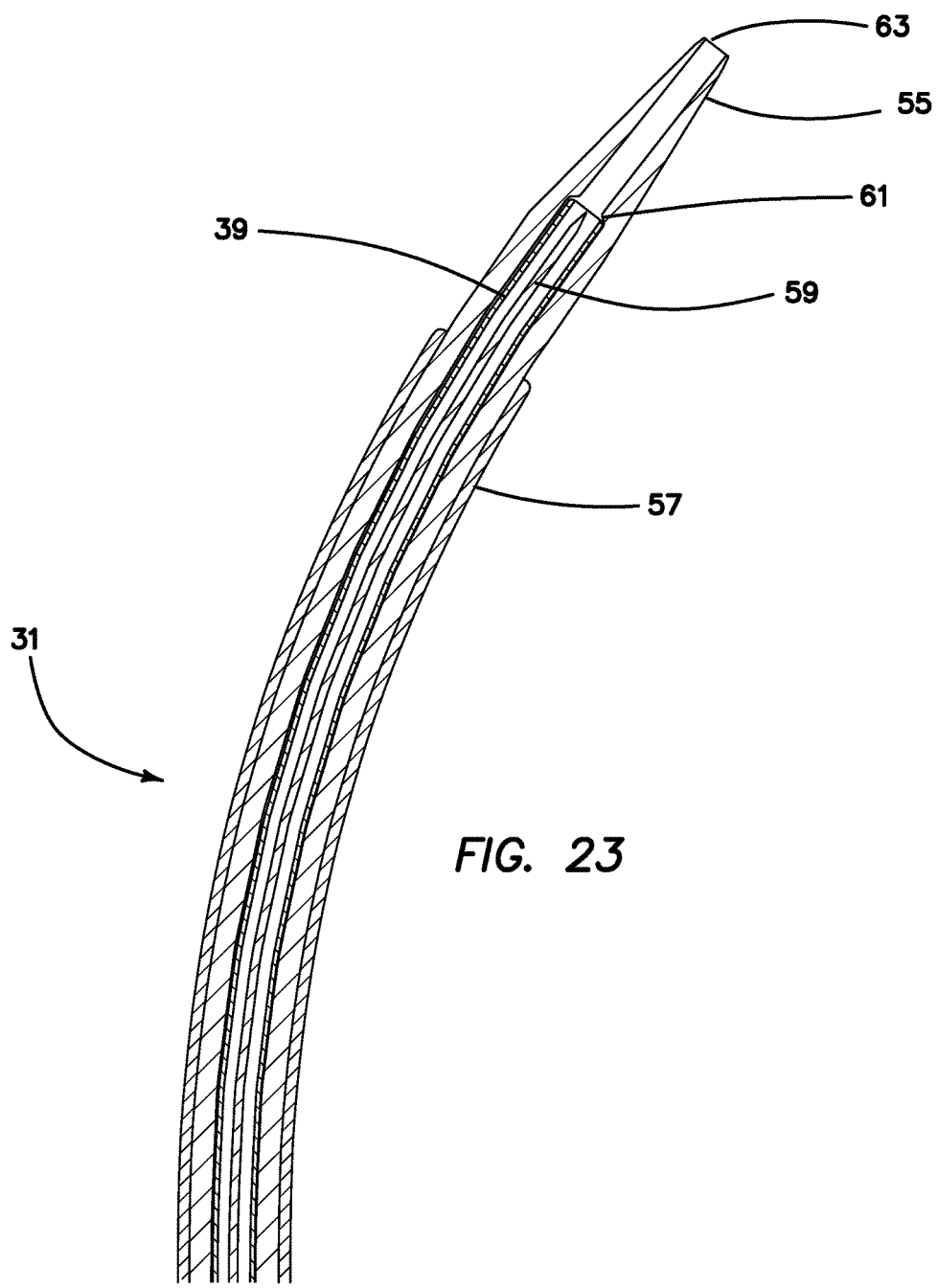
FIG. 23 shows the distal portion of the introducer assembly of FIG. 22 in which the cannula has been advanced to a distal internal stop in the dilator carrying the sharp tip guidewire with it.

FIG. 23 shows the distal portion of the introducer assembly 31 of FIG. 22 in enlarged scale in which the cannula 39 has been advanced to a distal internal stop 61 in the dilator 55 carrying the sharp tip guidewire 59 with it. In this embodiment the cannula 39 cannot be advanced out of and beyond the distal end 63 of the blunt end dilator 55.

Figure 24:
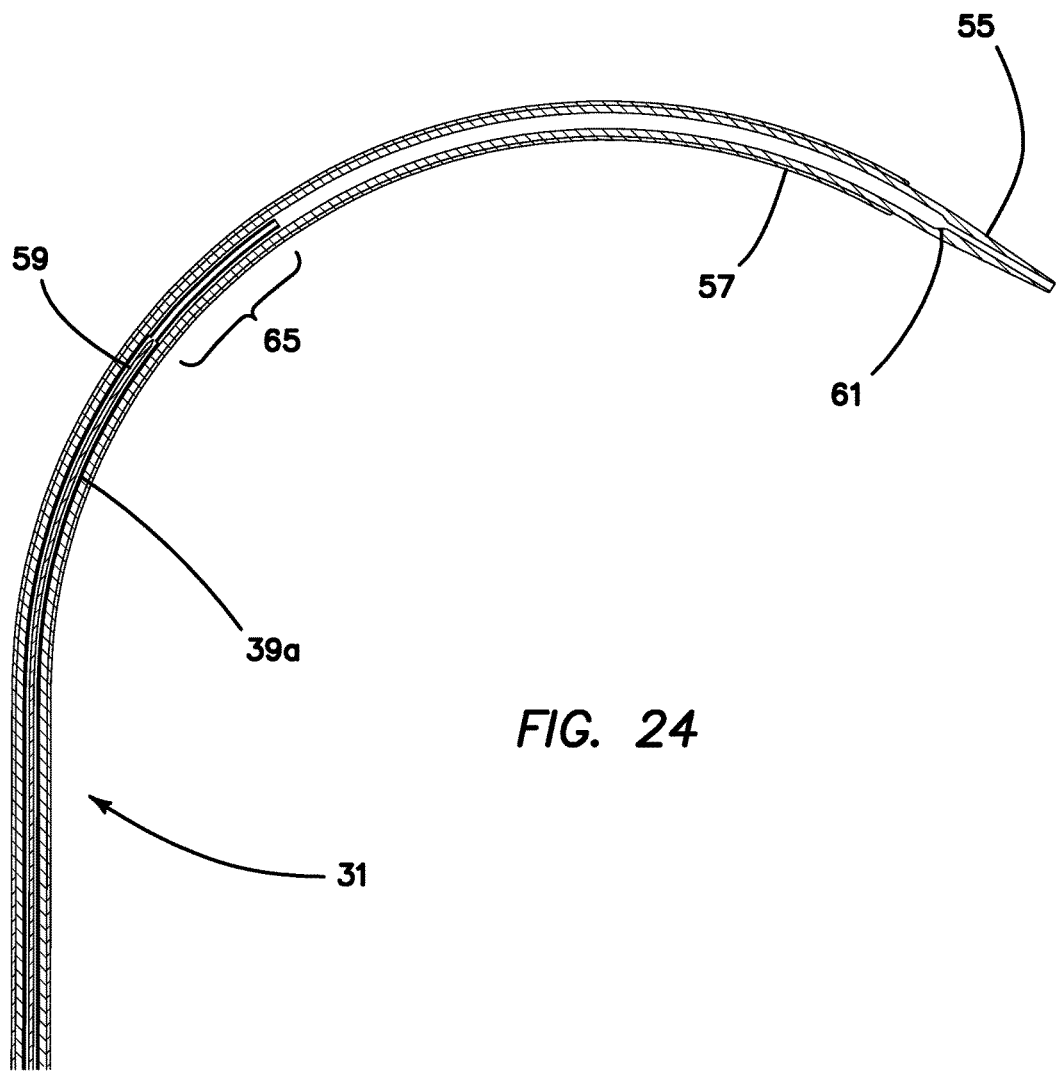
FIG. 24 is a side cross sectional view of the introducer assembly in enlarged scale showing the blunt end dilator extending from the end of the introducer sheath and the cannula and guidewire disposed in the dilator in a more proximal position in the embodiment where the cannula has a stepped-down outer diameter which will allow it to extend past the internal distal stop in the blunt end dilator.

FIG. 24 is a side cross sectional view of another embodiment of the introducer assembly 31 in enlarged scale showing the blunt end dilator 55 extending from the end of the introducer sheath 57 and a tapered cannula 39a and guidewire 59 disposed in the dilator 55 in a more proximal position in the embodiment where the cannula has a portion 65 with a stepped-down or tapered outer diameter which will allow it to extend past the internal distal stop 61 in the blunt end dilator 55. It is also conceived that a stylet (not shown) may be used with the tapered cannula 39a in place of the sharp tip guidewire 59, especially for placement of the tapered cannula 39a through the dilator 55. A stylet (not shown) is useful as an obturator for the tapered cannula 39a as well as to prevent any skiving of the dilator 55 when the tapered cannula 39a is advanced through the curved portion. The stylet (not shown) may lock onto the proximal hub 43 (FIG. 20a) of the cannula assembly 34 (FIG. 20a) and may be made of metal, polymer, composite, or glass, though preferably from stainless steel or nickel titanium alloy. The distal end of the stylet may also be tapered or necked down so as to fit through the distal necked down or tapered portion 65 of the tapered cannula 39a.

Figure 25:
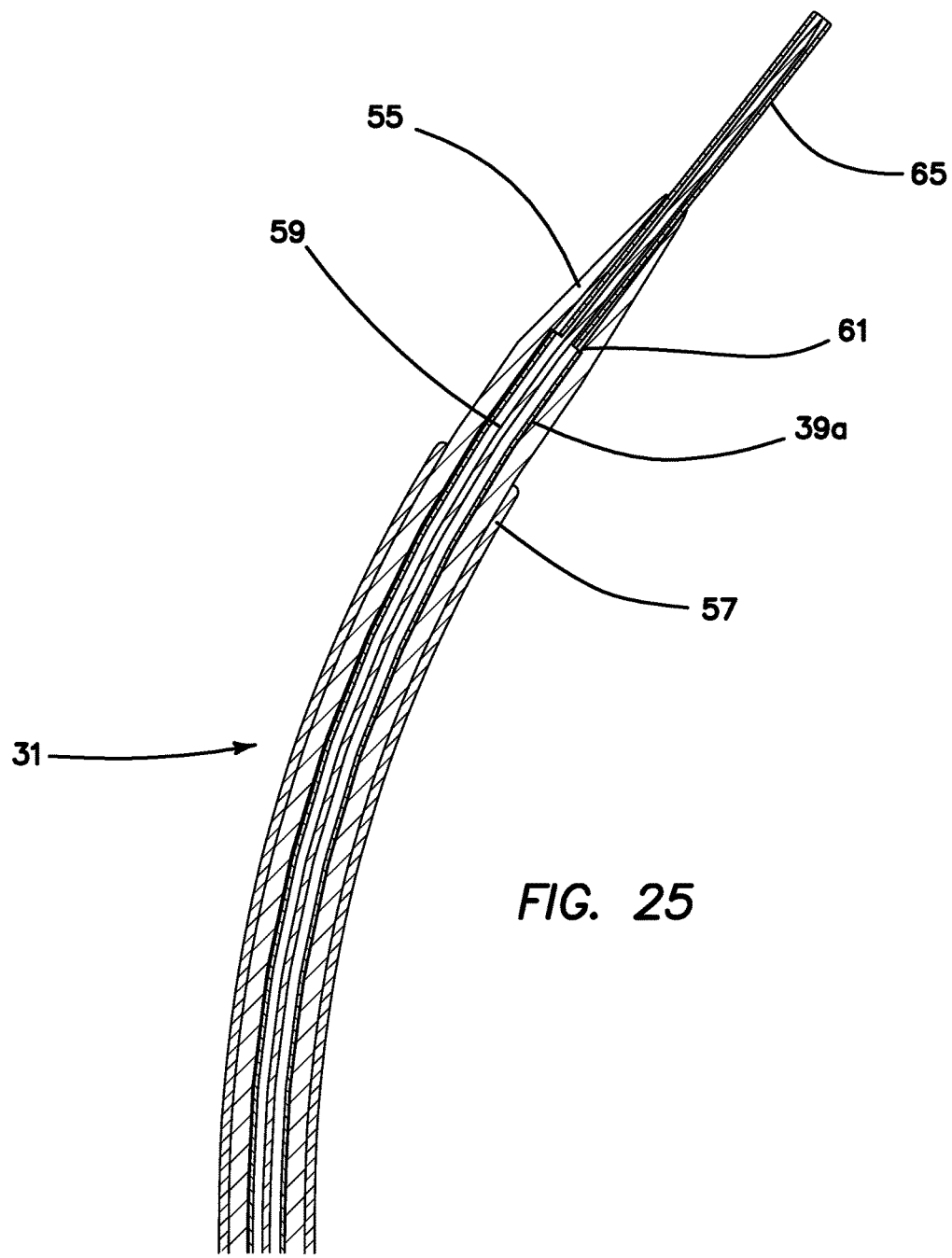
FIG. 25 shows the distal portion of the introducer assembly of FIG. 24 in which the cannula has been advanced past the distal internal stop in the dilator, extending from the distal end the blunt end dilator and carrying the sharp tip guidewire within it.

FIG. 25 shows the distal portion of the introducer assembly 31 of FIG. 24 in enlarged scale in which the cannula 39a has been advanced past the distal internal stop 61 in the dilator 55, extending from the distal end 63 the blunt end dilator 55 and carrying the sharp tip guidewire 59 within it.

The foregoing features can now be understood with respect to their operation and utility in the heart to effect a transseptal penetration using an introducer assembly 31 by viewing FIGS. 26-34 in the sequence described below for both the untapered and tapered cannulas 39 and 39a respectively. FIG. 26 shows the curved introducer assembly 31 in the configuration of FIG. 22 with the untapered cannula 39 within the atrium of the heart with the blunt end dilator 55 at or near a lower point on the septal wall 67 distant from the target location at which septal penetration is desired. The cannula 39 is not proximate to the dilator tip 63 so the final intended shape has not been imparted to introducer assembly 31 by cannula 39 carrying guidewire 59.

FIG. 27 shows the introducer assembly 31 of FIG. 26 in which the cannula 39 carrying the guidewire 59 has been advanced within introducer assembly 31 until the distal end 69 of the cannula 39 abuts the internal distal stop 61 in the blunt end dilator 55, showing how the cannula 39 gives a predetermined desired shape to the introducer assembly 31 to bring the tip 63 of blunt end dilator 55 to the desired position on the septal wall 67 where penetration is desired and to allow the steerability of introducer assembly 31 so that it can be manipulated or steered as desired. At this point the introducer assembly 31 can be advanced as a whole to tent the septal wall 67 prior to penetration.

FIG. 30 shows the curved introducer assembly 31 of FIG. 22 with the untapered cannula 39 in the desired position on the septal wall 67 with the sharp tip guide wire 59 advanced from the distal end 63 of the blunt end dilator 55, across and through the septal wall 67 into the opposing chamber 71 in the heart. The guidewire 59 has a distal curvature 73 that bends back on itself to present a nontraumatic shape. Any advancement of guidewire 59 therefore will not result in further penetration into cardiac tissue.

FIG. 32 is a side cross sectional view of the introducer assembly 31 of FIG. 30 after the blunt end dilator 55 and introducer sheath 57 have been advanced over the guidewire 59 with its atraumatic distal bend 73 through the septal wall 67 and into the opposing heart chamber 71. Cannula 39 in this embodiment is necessarily retained within the dilator 55 and may or may not be located in chamber 71 depending on the degree of advance of introducer assembly 31 as a whole.

FIG. 28 is a side cross sectional view of the introducer assembly 31 of FIG. 24 showing the blunt end dilator 55 extending from the end of the introducer sheath 57 and the cannula 39a and guidewire 59 disposed in the dilator 55 in a more proximal position in the embodiment where the cannula 39a has a portion 65 which has a stepped-down or tapered outer diameter which will allow it to extend past the internal distal stop 61 in the blunt end dilator 55.

FIG. 29 shows the introducer assembly 31 of FIG. 28 in which the stepped-down cannula 39a carrying the guidewire 59 has been advanced through the internal distal stop 61 in the blunt end dilator 55, showing how the cannula 39a gives a predetermined desired shape to the introducer assembly to bring the blunt end cannula 39a to the desired position on the septal wall 67 where penetration is desired and to provide the needed steerability and column strength to do so. Again at this point in the procedure introducer assembly 31 can be advanced as a whole to tent septal wall 67 prior to and during penetration.

FIG. 31 shows the curved introducer assembly of FIG. 29 in the desired position on the septal wall 67 with the sharp tip guide wire 59 advanced from the distal end 63 of the blunt end dilator 55, across and through the septal wall 67 into the opposing chamber 71 in the heart. The guidewire 59 has a distal curvature 73 that bends back on itself to present a nontraumatic shape. The stepped-down cannula 39a has been advanced to the distal end 63 of the blunt end dilator 55, but not beyond its distal tip 63.

FIG. 33 is a side cross sectional view of the introducer assembly 31 of FIG. 31 after the blunt end cannula 39a has been advanced over the guidewire 59 through the septal wall 67 and into the opposing heart chamber 71. The introducer sheath 57, and dilator 55 are not at this point yet advanced through the septal wall 67.

FIG. 34 is a side cross sectional view of the introducer assembly 31 of FIG. 33 after the blunt end cannula 39a, blunt end dilator 55 and introducer sheath 57 have been advanced over the guidewire 59 through the septal wall 67 and into the opposing heart chamber 71. The extent of advancement of cannula 39a, dilator 55 and sheath 57 into chamber 71 is variable and determined according to the physician's choice.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method comprising:
    telescopically disposing a blunt end cannula into a flexible introducer having an interior lumen, a distal curve, and a distal taper to define a predetermined shape and steerability to at least a distal portion of the introducer, where the flexible introducer has insufficient columnar strength and a shape ill-adapted for accessing a selected location on the cardiac septal wall of a patients heart when the cannula is not disposed within the interior lumen of the introducer and in dose proximity to the distal taper thereof, but is adapted to access the predetermined location on the cardiac septal wall when the cannula is disposed within the interior lumen of the introducer and in dose proximity to the distal taper thereof;
    intravascularly accessing a right, atrium of a patient's heart with the introducer;
    steering the distal taper of the introducer to the selected location on a septal wall of the heart to tent the septal wall at the selected location;
    advancing a sharp ended floppy guidewire telescopically disposed within an interior lumen of the cannula while being supported by the cannula to provide sufficient columnar strength to the floppy guidewire to allow it to be pushed through the septal wall into a left atrium of the patients heart; and
    advancing the sharp ended floppy guidewire beyond any support by the cannula to configure the sharp ended floppy guidewire into a prebiased atraumatic shape.

2. The method of claim 1 further comprising advancing the cannula through the septal wall over the guidewire.

3. The method of claim 2 further comprising advancing the introducer through the septal wall over the cannula.

4. The method of claim 1 further comprising advancing the introducer through the septal wall over the guidewire while leaving the cannula telescopically retained in the introducer.

5. The method of claim 1 where intravascularly accessing a right atrium of the patient's heart with the introducer comprises accessing the right atrium through a femoral vein.

6. The method of claim 1 where intravascularly accessing a right atrium of the patient's heart with the introducer comprises accessing the right atrium through a superior vena cava.

7. The method of claim 1 further comprising steering the distal taper of the introducer to a fossa ovalis using the blunt end cannula.

8. The method of claim 1 further comprising advancing the cannula through the septal wall over the sharp ended floppy guidewire.

9. A method comprising:
    telescopically disposing a blunt end cannula into a flexible introducer having an interior lumen, a distal curve, and a distal taper to define a predetermined shape and steerability to at least a distal portion of the introducer, where the flexible introducer has insufficient columnar strength and a shape ill-adapted for accessing a selected location on a patient's tissue when the blunt end cannula is not disposed within the interior lumen of the introducer and in close proximity to the distal taper thereof, but is adapted to access the predetermined location on the patient's tissue when the blunt end cannula is disposed within the interior lumen of the introducer and in close proximity to the distal taper thereof;
    providing a channel through the cannula in which to dispose an elongated medical device into the patient's heart;
    providing sufficient columnar strength to the elongated medical device using the cannula to allow the elongated medical device to provide force against or push through the cardiac septal wall into the patient's heart;
    intravascularly accessing the patient's tissue with the introducer; and
    steering the distal taper of the introducer to the selected location on the patient's tissue to engage the tissue at the selected location.

10. The method of claim 9 where intravascularly accessing the patient's tissue with the introducer comprises accessing the cardiac septal wall of the patient's heart.

11. The method of claim 10 where intravascularly accessing the patient's heart with the introducer comprises accessing the right atrium through a femoral vein.

12. The method of claim 10 where intravascularly accessing the patient's heart with the introducer comprises accessing the right atrium through a superior vena cava.

13. The method of claim 9 further comprising advancing the elongated medical device beyond any support provided by the cannula while leaving the cannula retained in the introducer.

14. The method of claim 9 further comprising steering the distal taper of the introducer to a fossa ovalis using the cannula.

15. A method comprising:
    telescopically disposing a blunt end cannula into a flexible introducer having an interior lumen, a distal curve, and a distal taper to define a predetermined shape and steerability to at least a distal portion of the introducer, where the flexible introducer has insufficient columnar strength and a shape ill-adapted for accessing a selected location of a patient's tissue when the cannula is not disposed within the interior lumen of the introducer and in close proximity to the distal taper thereof, but is adapted to access the predetermined location on the patient's tissue when the cannula is disposed within the interior lumen of the introducer and in close proximity to the distal taper thereof;
    intravascularly accessing a patient's tissue with the introducer;
    steering the distal taper of the introducer to the selected location on a patient's tissue at the selected location to engage the tissue;
    advancing a sharp ended floppy guidewire telescopically disposed within an interior lumen of the cannula while being supported by the cannula to provide sufficient columnar strength to the floppy guidewire to allow it to be pushed through the patient's tissue; and advancing the sharp ended floppy guidewire beyond any support by the cannula to configure the sharp ended floppy guidewire into a prebiased atraumatic shape.

16. A method comprising:

telescopically disposing a blunt end cannula into a flexible introducer having an interior lumen, a distal curve, and a distal taper to define a predetermined shape and steerability to at least a distal portion of the introducer, where the flexible introducer has insufficient columnar strength and shape for accessing a selected location on a patient's tissue when the blunt end cannula is not positioned within the interior lumen of the introducer and in close proximity to the distal taper thereof, but is able to access the predetermined location on the patient's tissue when the blunt end cannula is disposed within the interior lumen of the introducer and in close proximity to the distal taper thereof;

intravascularly accessing the patient's tissue with the introducer;

steering the distal taper of the introducer to the selected location on the patient's tissue to engage the tissue at the selected location;

providing a channel through the cannula in which to dispose an elongated medical device into the patient's heart; and providing sufficient columnar strength to the elongated medical device using the cannula to allow the elongated medical device to provide force against or push through the cardiac septal wall into the patient's heart.

17. The method of claim 16 where intravascularly accessing the patient's tissue with the introducer comprises accessing the cardiac septal wall of the patient's heart.

18. The method of claim 17 where intravascularly accessing the patient's heart with the introducer comprises accessing the right atrium through a femoral vein.

19. The method of claim 17 where intravascularly accessing the patient's heart with the introducer comprises accessing the right atrium through a superior vena cava.

20. The method of claim 16 further comprising providing sufficient columnar strength to the elongated medical device using the cannula to allow the elongated medical device to provide force against or push through the cardiac septal wall into the patient's heart.

21. The method of claim 16 further comprising steering the distal taper of the introducer to a fossa ovalis using the cannula.

* * * * *